United States Patent
Roos et al.

(10) Patent No.: US 11,911,424 B2
(45) Date of Patent: *Feb. 27, 2024

(54) SELECTION AND USE OF MELATONIN SUPPORTING BACTERIA TO REDUCE INFANTILE COLIC

(71) Applicant: BioGaia AB, Stockholm (SE)

(72) Inventors: Stefan Roos, Uppsala (SE); Bo Möllstam, Lerum (SE)

(73) Assignee: BioGaia AB, Stockholm (SE)

( * ) Notice: Subject to any disclaimer, the term of this patent is extended or adjusted under 35 U.S.C. 154(b) by 767 days.

This patent is subject to a terminal disclaimer.

(21) Appl. No.: 16/961,598

(22) PCT Filed: Jul. 24, 2019

(86) PCT No.: PCT/EP2019/069984
§ 371 (c)(1),
(2) Date: Jul. 10, 2020

(87) PCT Pub. No.: WO2020/020982
PCT Pub. Date: Jan. 30, 2020

(65) Prior Publication Data
US 2022/0347237 A1    Nov. 3, 2022

(30) Foreign Application Priority Data

Jul. 24, 2018 (GB) .................................... 1812079
Apr. 17, 2019 (GB) .................................... 1905470

(51) Int. Cl.
*A61K 35/747* (2015.01)
*A61P 25/28* (2006.01)
(Continued)

(52) U.S. Cl.
CPC .............. *A61K 35/747* (2013.01); *A61P 5/00* (2018.01); *A61P 25/28* (2018.01); *C12N 1/205* (2021.05);
(Continued)

(58) Field of Classification Search
CPC .......... A61K 35/747; A61P 5/00; A61P 25/28; C12N 1/205; C12P 17/165; C12P 19/40; C12R 2001/225; C12Y 301/03031
See application file for complete search history.

(56) References Cited

U.S. PATENT DOCUMENTS

2007/0280913 A1    12/2007    Connolly et al.
2008/0058405 A1    3/2008     Lewy
(Continued)

FOREIGN PATENT DOCUMENTS

CN    104918640 A    9/2015
CN    108029923 A    5/2018
(Continued)

OTHER PUBLICATIONS

Talarico, T. L., et al. "Production and isolation of reuterin, a growth inhibitor produced by Lactobacillus reuteri." Antimicrobial agents and chemotherapy 32.12 (1988): 1854-1858. (Year: 1988).*
(Continued)

*Primary Examiner* — Lora E Barnhart Driscoll
*Assistant Examiner* — Candice Lee Swift
(74) *Attorney, Agent, or Firm* — McNeill Baur PLLC

(57) ABSTRACT

The present invention relates to lactic acid bacterial strains which are capable of producing or inducing the production of melatonin, for use in the production of melatonin in a subject. Preferred strains for such uses are capable of producing or inducing the production of adenosine. Therapeutic uses of such strains include the treatment or preven-
(Continued)

tion of diseases associated with melatonin deficiency, for example infantile colic. Novel strains are also provided.

16 Claims, 5 Drawing Sheets

Specification includes a Sequence Listing.

(51) Int. Cl.
- *A61P 5/00* (2006.01)
- *C12N 1/20* (2006.01)
- *C12P 17/16* (2006.01)
- *C12P 19/40* (2006.01)
- *C12R 1/225* (2006.01)

(52) U.S. Cl.
CPC ............. *C12P 17/165* (2013.01); *C12P 19/40* (2013.01); *C12R 2001/225* (2021.05); *C12Y 301/03031* (2013.01)

(56) References Cited

U.S. PATENT DOCUMENTS

| | | |
|---|---|---|
| 2013/0273015 A1 | 10/2013 | Klassen et al. |
| 2014/0363409 A1 | 12/2014 | Degonda et al. |
| 2016/0334391 A1 | 11/2016 | Conolly et al. |
| 2017/0216375 A1 | 8/2017 | Möllstam et al. |
| 2017/0368112 A1 | 12/2017 | Erdman |
| 2021/0060098 A1 | 3/2021 | Roos et al. |
| 2023/0057324 A1 | 2/2023 | Roos et al. |

FOREIGN PATENT DOCUMENTS

| | | | |
|---|---|---|---|
| EP | 2609813 | A1 | 7/2013 |
| EP | 2674162 | A1 | 12/2013 |
| KR | 100913405 | B1 | 8/2009 |
| KR | 100913406 | B1 | 8/2009 |
| RU | 2435844 | C2 | 12/2011 |
| RU | 2642301 | C2 | 1/2018 |
| WO | 2007142596 | A1 | 12/2007 |
| WO | 2010060722 | A1 | 6/2010 |
| WO | 2013144701 | A1 | 10/2013 |
| WO | 2013153358 | A1 | 10/2013 |
| WO | 2014033330 | A1 | 3/2014 |
| WO | 2015112083 | A1 | 7/2015 |
| WO | 2015177246 | A2 | 11/2015 |
| WO | 2016002757 | A1 | 1/2016 |
| WO | 2016102660 | A1 | 6/2016 |
| WO | 2016153422 | A1 | 9/2016 |
| WO | 2017203048 | A1 | 11/2017 |
| WO | 2020020984 | A1 | 1/2020 |

OTHER PUBLICATIONS

Klein, David C. "Arylalkylamine N-acetyltransferase:"the Timezyme"." Journal of biological chemistry 282.7 (2007): 4233-4237. (Year: 2007).*

Jensen H, Roos S, Jonsson H, Rud I, Grimmer S, van Pijkeren JP, Britton RA, Axelsson L. Role of Lactobacillus reuteri cell and mucus-binding protein A (CmbA) in adhesion to intestinal epithelial cells and mucus in vitro. Microbiology (Reading). Apr. 2014;160(Pt 4):671-681. (Year: 2014).*

Pang, Yanhong, et al. "Extracellular membrane vesicles from Limosilactobacillus reuteri strengthen the intestinal epithelial integrity, modulate cytokine responses and antagonize activation of TRPV1." Frontiers in Microbiology 13 (2022): 1032202. (Year: 2022).*

Liu, Yuying, et al. "Probiotic-derived ecto-5′-nucleotidase produces anti-inflammatory adenosine metabolites in Treg-deficient scurfy mice." Probiotics and Antimicrobial Proteins (2023): 1-13. (Year: 2023).*

Kegg; https://www.genome.jp/entry/3.1.3.5; accessed Jun. 26, 2023 (Year: 2023).*

English Translation of Chinese Office Action issued in Application No. 201980036257.3, dated Aug. 11, 2022, 11 pages.

Database WPI Week 200962 Thomson Scientific, London, GB; An 2009-N32996 XP002773575, & KR 100 913 405 BI (Gwangju Inst Sci&Technology) Aug. 21, 2009 (Aug. 21, 2009) abstract.

Database WPI Week 200962 Thomson Scientific, London, GB; An 2009-N32997 XP002773576, & KR 100 913 406 BI (Gwangju Inst Sci&Technology) Aug. 21, 2009 (Aug. 21, 2009) abstract.

Fei, Li, "Excessive Crying of Infants", Chinese Journal of Child Health Care, No. 6, pp. 564-566 (2016).

He et al., "Resetting microbiota by Lactobacillus reuteri inhibits T reg deficiency-induced autoimmunity via adenosine A2A receptors", The Journal of Experimental Medicine, (214)(1), pp. 1-17 (2016).

International Depository Authority DSM 33198 dated Jul. 9, 2019; Viability Statement DSM 33198 dated Jul. 9, 2019; 2 pages.

Karimi et al., "Foxp3+CD4+ Regulatory T cells Induced by Oral Treatment with Lactobacillus reuteri Protect Against Experimentally Induced Asthma in Mice", Clinical Journal of Allergy and Immunology, (121)(2), (2008).

Karimi et al., "Lactobacillus reuteri-induced Regulatory T cells Protect against an Allergic Airway Response in Mice", American Journal of Respiratory and Critical Care Medicine, (179)(3), pp. 186-193 (2009).

Ledesma-Amaro et al., "Increased production of inosine and guanosine by means of metabolic engineering of the burine pathway in Ashbya gossypii", Microbial Cell Factories, 14:58, i (2015).

Liu et al., "Lactobacillus reuteri strains reduce incidence and severity of experimental necrotizing enterocolitis via modulation of TLR4 and NF-κB signaling in the intestine", Am J Physiol Gastrointest Liver Physiol. Mar. 15, 2012; 302(6): G608-G617.

Liu et al., "Oral Feeding Lactobacillus Reuteri DSM17938 Reduces Inflammation in Lungs of Treg-Deficient Scurfy Mice", URL:http://www.gastrojournal.org/article/S 0016-5085(15)31778-9/pdf; (2015) (abstract).

Long et al., "Periodic Syndromes that may be associated with migraine," Chinese Journal of Pain Medicine, No. 2, pp. 126-129 (2018).

International Depository Authority DSM 17938, dated Feb. 6, 2006; Viability Statement for DSM 17938 dated Feb. 6, 2006; 2 pages.

International Search Report and Written Opinion issued in International Application No. PCT/EP2019/069984, dated Dec. 13, 2019; 20 pages.

International Search Report and Written Opinion issued in International Application No. PCT/EP2019/069987, dated Oct. 28, 2019; 19 pages.

Kilstrup, et al., "Nucleotide metabolism and its control in lactic acid bacteria," FEMS Microbiology Reviews, Elsevier, Amsterdam, vol. 29, No. 3, p. 555-590 (2005).

Lukic et al., "Probiotics or pro-healers: the role of beneficial bacteria in tissue repair: The role of probiotics in wound healing," Wound Repair and Regeneration, vol. 25, No. 6, p. 912-922 (2017).

Ruiz et al., "Bile resistance mechanisms in Lactobacillus and Bifidobacterium", Frontiers in Microbiology, vol. 4, (2013).

Sung et al., "Treating infant colic with the probiotic Lactobacillus reuteri:double blind, placebo controlled randomised trial.," BMJ, vol. 348, No. Apr. 1 2002, p. g2107-g2107 (2014).

Tolga et al., "The role of melatonin and cortisol circadian rhythms in the pathogenesis of infantile colic," World Journal of Pediatrics, Hangzhou Institute of Pediatrics: Springer, CN, vol. 14, No. 4, p. 392-398, (2018).

Vagesjo et al., "Accelerated wound healing in mice by on-site production and delivery of CXCL12 by transformed lactic acid bacteria." PNAS, vol. 115, No. 8, p. 1895-1900 (2018).

International Depository Authority DSM 32846 dated Jul. 4, 2018; Viability Statement for DSM 32846 dated Jul. 4, 2018; 4 pages.

International Depository Authority DSM 32847 dated Jul. 4, 2018; Viability Statement for DSM 32847 dated Jul. 4, 2018; 4 pages.

International Depository Authority DSM 32848 dated Jul. 4, 2018; Viability Statement for DSM 32848 dated Jul. 4, 2018; 4 pages.

(56) References Cited

OTHER PUBLICATIONS

International Depository Authority DSM 32849 dated Jul. 4, 2018; Viability Statement for DSM 32849 dated Jul. 4, 2018; 4 pages.
International Depository Authority DSM 33198 dated Jul. 9, 2019; Viability Statement for DSM 33198 dated Jul. 9, 2019; 2 pages.
Ardatskaya et al., "Colon dysbacteriosis (dysbiosis): modern state of the problem, comprehensive diagnosis and treatment correction," Experimental and clinical gastroenterology,117 (5): 13-50 (2015).
He et al., "Adenosine A2A receptor deletion blocks the beneficial effects of Lactobacillus reuteri in regulatory T-deficient scurfy mice," Frontiers in Immunology, vol. 8, Article 1680, p. 1-9 (2017).
Santosh et al. "Role of Adenosine Deaminase in Common Chronic ENT Infections", Mar. 2016, Journal of Clinical and Diagnostic Research, vol. 10(3): MC01-MC02 (2016).
Savino et al., "Crying Time and RORγ/FOXP3 Expression in Lactobacillus reuteri DSM17938-Treated Infants with Colic: A Randomized Trial," The Journal of Pediatrics vol. 192, pp. 171-177.e1 (2018).
Sung et al., "Lactobacillus reuteri to Treat Infant Colic: A Meta-analysis," Pediatrics. 141(1):e20171811 (2018).
Vinderola et al. "Correlation between in vitro and in vivo assays in selection of probiotics from traditional species of bacteria", Trends in Food Science & Technology, vol. 68, p. 83-90. (2017).

\* cited by examiner

*The rate of melatonin formation depends on the activity of enzymes AANAT and to a lesser extent of TPH*

*Adenosine increases intracellular cAMP levels via adenosine receptor, which increases the production of AANAT, the rate limiting enzyme in melatonin synthesis.*

5'-nucleotidase activity. Analysis of supernatants of bacterial cultures with the concentration $10^9$ bacteria per ml

A

B

SELECTION AND USE OF MELATONIN SUPPORTING BACTERIA TO REDUCE INFANTILE COLIC

This application is a national phase entry pursuant to 35 U.S.C. § 371 of International Application No. PCT/EP2019/069984, filed Jul. 24, 2019, which claims the benefit of GB Application No. 1812079.0, filed Jul. 24, 2018 and GB Application No. 1905470.9, filed Apr. 17, 2019, each of which is incorporated by reference herein in its entirety.

FIELD OF THE INVENTION

The invention herein provides certain strains of lactic acid bacteria selected for their ability of increasing melatonin levels for prophylaxis and/or treatment of colic (or other diseases associated with reduced levels of melatonin), including the ability to produce precursors and other important components for melatonin release, a method of selecting such strains, and products containing such strains. Moreover this invention relates to preparations comprising substrate components being specifically chosen to enhance the efficacy of such strains.

SEQUENCE LISTING

The present application is filed with a Sequence Listing in electronic format. The Sequence Listing file was created on Jan. 14, 2021, is entitled "2021-01-14_01189-000600US_Seq_List_ST25.txt," and is 11,220 bytes in size. The information in the electronic format of the sequence listing is incorporated herein by reference in its entirety.

BACKGROUND OF THE INVENTION

Despite its salience in terms of both prevalence and distress the nature and causes of infantile colic have remained poorly understood. There are also different terms used to describe the condition. These terms include, "infantile colic", "evening colic" because the pain is mainly confined to evening, and "three months colic" under the pretext that it disappears after about three months after birth. Different authors have used different definitions. The definition of Wessels that colic is paroxysms of crying for three or more hours per days for three days or more per week during a period of at least three weeks has been mostly accepted in the literature. In 2006, the Rome III criteria was published modifying this criteria to consider the diagnosis of "infantile colic" applicable to infants with paroxysms of irritability, fussing, or crying that start and stop without obvious cause, lasting 3 or more hours per day and occurring at least 3 days per week, but for at least 1 week (sometimes referred to as modified Wessel's criteria). Further fine-tuned in the Rome IV criteria; (Benninga et al; Gastroenterology 2016; 150:1443-1455). Either of these definitions (Rome III or Rome IV) is relevant to the present invention.

To date, the main discussed possible causative factors of infantile colic have been divided into: psychosocial, gastrointestinal, including microbial dysbiosis, and neuro-developmental disorders.

Psychosocial factors include: variants of normal crying, behavioural effects of atypical parenting and manifestation of problems in parent-infant interaction.

Gastrointestinal disorders have been implicated in colic because of the infant's leg position and grimacing during a crying spell. The gastrointestinal factors are briefly reviewed below:

Improper feeding techniques like bottle feeding, feeding in a horizontal position and lack of burping post-feeding have been considered as causative factors. Breast-feeding in the first six months has been found to be protective factor. The risk of infantile colic is 1.86 times higher among non-breast fed infants (Saavedra M A, Dacosta J S, Garcias G, Horta B L, Tomasi E, Mendoca R. Infantile colic incidence and associated risk factors: a cohort study. Pediatr (Rio J) 2003; 79(2): 115-122).

At present there is no complete cure for colic. The current treatment paradigm for colic consists of either pharmacological and/or non-pharmacological methods, providing at best reduction of symptoms. Typical therapeutic interventions for colic offered to parents fall within four categories, including, dietary, physical, behavioral and pharmacological. Dietary manipulations include professional advice on various feeding techniques, or the use of hypoallergenic milk, soy or lactose free formulas, food supplements such as various probiotics and prebiotics and an early introduction to solids.

A non-prescription medication for treatment of colic has largely included the administration of simethicone or dimethylpolysiloxane, a non-absorbable, over-the-counter drug, which reduces the size of intestinal gas bubbles. Simethicone has a safe profile and is frequently recommended, despite several studies demonstrating that effectiveness of Simethicone on infantile colic is no better than placebo.

There have been some reports implicating an altered microbiota-pattern in colicky infants, making several researchers to perform and publish different randomized clinical controlled trials (RCTs) where the ability of for example *Lactobacillus reuteri* DSM 17938 to reduce crying time in these infants has been evaluated. For example, Savino et al (Pediatrics 2010; 126:e526-33) conducted an RCT in 2010 to test the efficacy of this strain on infantile colic. Fifty exclusively breastfed colicky infants, diagnosed according to modified Wessel's criteria, were randomly assigned to receive either *L. reuteri* DSM 17938 ($10^8$ colony-forming units) or placebo daily for 21 days. Parental questionnaires monitored daily crying time and adverse effects. Forty-six infants (*L. reuteri* group: 25; placebo group: 21) completed the trial. Daily crying times in minutes/day (median) were 370 vs 300 on day 0 and 35.0 vs 90.0 ($p=0.022$) on day 21.

In 2013 Szajewska et al (J Pediatr 2013; 162:257-62) published with a similar design an RCT in 80 infants aged<5 months, identifying that the rate of responders to treatment was significantly higher in the probiotic group compared with the placebo group. Minutes/day (median) were 180 vs 180 on day 7, 75 vs 128 on day 14 and 52 vs 120 ($p<0.05$) on day 21. There have also been several other studies showing the effect of *L. reuteri* DSM 17938 in colicky infants in significantly reducing crying-time in breastfed infants. There is however a need for even more effective interventions to reduce the crying at a higher rate in children with colic, including at a higher rate in formula-fed children.

Therefore, there currently is a need for new (and preferably improved) safe and effective compounds and compositions and techniques that prove useful for treating colic in infants. The compositions and methods of the present invention, respond to this need, providing products that can safely and effectively prevent and treat colic (or the symptoms associated with colic) in infants.

Other objects and advantages will be more fully apparent from the following disclosure.

SUMMARY OF THE INVENTION

New-borns hormone immaturity is implicated to be a major factor in early problems of the development of gut motility and thereby also causing pain and crying of the infant, such as in infantile colic. Melatonin is a hormone that has the ability to support biological rhythms and has important effects on many functions in humans and animals. A precursor to melatonin is serotonin, a neurotransmitter itself that can be derived from the amino acid tryptophan.

Melatonin is a neurotransmitter previously thought to be secreted predominantly by the pineal gland. There are however extra-pineal sites of melatonin production, such as the retina and the gastrointestinal tract.

Synchronization between production and the different circadian rhythms and the following release of serotonin and melatonin in young infants is potentially important to avoid gut motility disturbances and pain, such as infantile colic (IC).

Serotonin increases intestinal smooth muscle contraction, and melatonin relaxes intestinal smooth muscles. The serotonin concentration peaks can cause intestinal cramps if not balanced by other agents, whereof melatonin is an important one. Both serotonin and melatonin have circadian rhythms. While there is serotonin produced and serotonin circadian rhythms developed when an infant is born, the endogenous melatonin production and melatonin circadian rhythm is in many infants not ready to begin until after the $3^{rd}$ month in life. This time coincides with the time of normal disappearance of infantile colic.

It can be said that infantile colic is a condition of melatonin-deficiency. It has therefore been suggested to give exogenous melatonin to infants with IC, but many physicians and parents are reluctant to give hormones to an infant.

Of all new-born children there is an estimated prevalence of 5% to 25% of IC which is in several ways burdensome and costly for society, the parents and the infant itself.

Thus, although some children appear able to produce and release needed melatonin from their food and/or their intestinal bacteria and are therefore less likely to develop infantile colic, there are many others who do not, and thus need added support to prevent or treat IC.

There is thus a need to find and develop products and methods to support melatonin production and release in children at risk of developing IC or having IC.

The present invention is based on the finding that bacteria, for example lactic acid bacteria, can be selected which are capable of producing adenosine. Lactic acid bacteria producing adenosine have not been reported in the art and such bacteria can for example be used to increase the production of arylalkylamine-N-acetyltransferase (AANAT), the rate-limiting enzyme in melatonin synthesis. Although the AANAT enzyme is found in the pineal gland it is also produced at the extra-pineal sites of melatonin production, such as in the gastrointestinal tract. Thus, an increase in AANAT production (for example via an increase in adenosine production) provides a means of increasing melatonin production or increasing melatonin levels in the gastrointestinal tract. Such bacteria can thus be used in the treatment or prevention of infantile colic or other diseases associated with or characterised by reduced, low or deficient melatonin production or synthesis.

Thus, the present invention provides a bacterial strain, e.g. a lactic acid bacterial strain which is capable of producing or inducing the production of adenosine, for use in the production of adenosine (e.g. increasing levels of adenosine or increasing or promoting the production of adenosine) in a subject, or for use in the production of melatonin (e.g. increasing levels of melatonin or increasing or promoting the production of melatonin) in a subject.

The present invention further provides a method for producing adenosine or melatonin (e.g. increasing levels of adenosine or melatonin, or increasing or promoting the production of adenosine or melatonin) in a subject, said method comprising the step of administering an effective amount of a bacterial strain, e.g. a lactic acid bacterial strain, which is capable of producing or inducing the production of adenosine, to said subject.

The present invention further provides the use of a bacterial strain, e.g. a lactic acid bacterial strain, which is capable of producing or inducing the production of adenosine, in the manufacture of a medicament or composition for use in the production of adenosine or melatonin (e.g. increasing levels of adenosine or melatonin, or increasing or promoting the production of adenosine or melatonin) in a subject.

Viewed more generally, the present invention also provides bacteria, for example lactic acid bacteria, which are capable of producing or inducing the production of melatonin. Such bacteria can thus be used for the production of melatonin, for example for increasing the production or levels of melatonin, in a subject.

Thus, in one aspect the present invention provides a lactic acid bacterial strain which is capable of producing or inducing the production of melatonin, for use in the production of melatonin (e.g. increasing levels of melatonin or increasing or promoting the production of melatonin) in a subject.

In another aspect, the present invention provides a method of producing melatonin (e.g. increasing levels of melatonin or increasing or promoting the production of melatonin) in a subject, said method comprising the step of administering an effective amount of a lactic acid bacterial strain which is capable of producing or inducing the production of melatonin to said subject.

In another aspect, the present invention provides the use of a lactic acid bacterial strain which is capable of producing or inducing the production of melatonin, in the manufacture of a medicament or composition for use in the production of melatonin (e.g. increasing levels of melatonin or increasing or promoting the production of melatonin) in a subject.

As discussed above, such strains can be used in the treatment or prevention of infantile colic, or other diseases associated with or characterised by reduced, low or deficient melatonin production or synthesis or levels.

Thus the invention further provides a lactic acid bacterial strain which is capable of producing or inducing the production of melatonin, for use in the treatment or prevention of infantile colic, or other diseases associated with or characterised by reduced, low or deficient melatonin production or synthesis or levels in a subject.

In another aspect, the present invention provides a method of treatment or prevention of infantile colic, or other disease associated with or characterised by reduced, low or deficient melatonin production or synthesis or levels, in a subject, said method comprising the step of administering an effective amount of a lactic acid bacterial strain which is capable of producing or inducing the production of melatonin to said subject.

In another aspect, the present invention provides the use of a lactic acid bacterial strain which is capable of producing or inducing the production of melatonin, in the manufacture of a medicament or composition for use in the treatment or prevention of infantile colic, or other disease associated with or characterized by reduced, low or deficient melatonin production or synthesis or levels, in a subject.

Such strains may be capable of producing or inducing the production of adenosine and thereby producing or inducing the production (for example downstream production) of melatonin as described elsewhere herein.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

Thus, as outlined above, the present invention provides, bacterial strains, e.g. lactic acid bacterial strains, which are capable of producing or stimulating or inducing or supporting the production of melatonin, for example to increase levels of melatonin, particularly in the gastrointestinal (GI) tract. Such strains may themselves produce melatonin, e.g. secrete melatonin, and thus provide or produce melatonin directly.

However, also provided, are strains which indirectly result in the production of melatonin, for example by producing or stimulating or inducing the production of an upstream component of the melatonin synthesis pathway (or a precursor of melatonin) and thereby supporting or increasing melatonin production. A preferred example would be the production or induction of arylalkylamine-N-acetyl transferase (AANAT), which is the rate limiting enzyme in the conversion of serotonin to N-acetyl serotonin, which in turn gets converted into melatonin.

Figure 2:
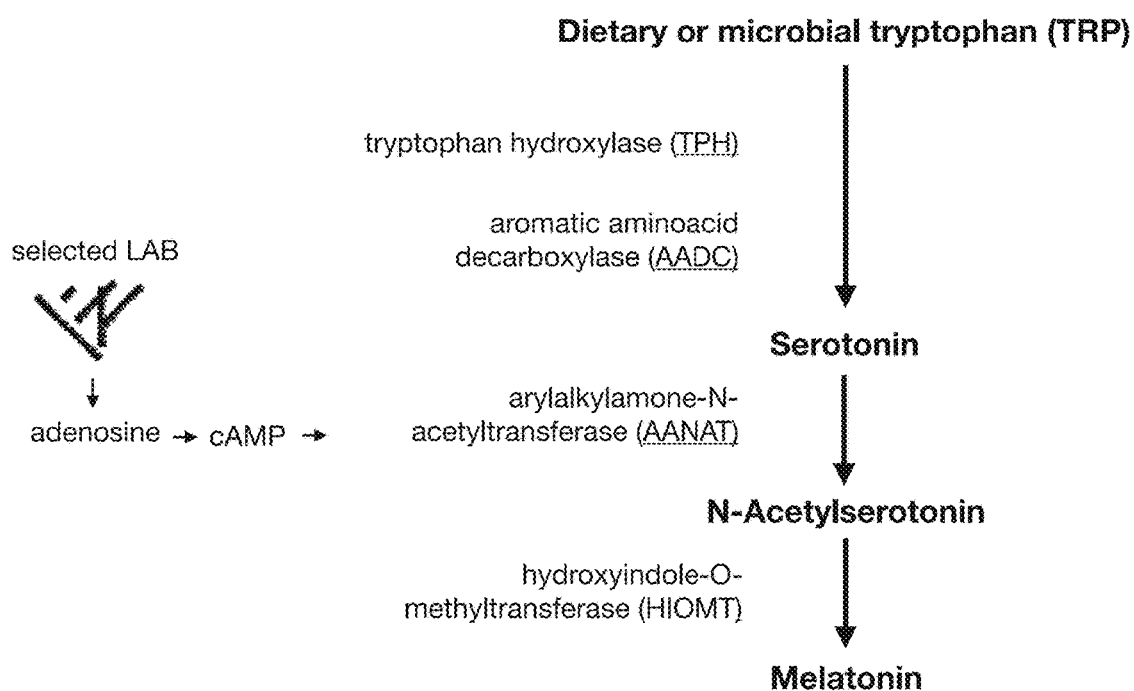
FIG. 2 is a schematic showing how a bacteria capable of producing adenosine of the invention affects the melatonin production pathway.

As outlined above, another particularly preferred lactic acid bacterial strain is one which can produce or induce adenosine in a subject, particularly in the gastrointestinal (GI) tract. Such adenosine can act on appropriate cell surface adenosine receptors (for example A2A receptors, A2B receptors, A3 or A4 receptors, preferably A2A receptors) and result in the production of elevated levels of intracellular cAMP. A2A and other adenosine receptors are known to be present in cells found in the GI tract. Intracellular cAMP in turn is involved in the production of AANAT (see FIG. 2). Thus, increased intracellular cAMP levels can result in increased AANAT levels and therefore increased melatonin levels. The adenosine should thus preferably be provided extracellularly in order to be able to bind to cell surface adenosine receptors. To this end, the adenosine may be produced within the bacterial cells and be transported extracellularly (or secreted). Alternatively the adenosine may be produced extracellularly, for example on the bacterial cell surface or in the supernatant. Such extracellular production can for example conveniently take place by way of the presence of a cell wall (or cell surface) anchored 5'-nucleotidase enzyme (or ecto 5'-nucleotidase enzyme), which can convert appropriate substrate to adenosine. Such extracellular production can equally take place by way of the presence of a 5'-nucleotidase enzyme (or ecto 5'-nucleotidase enzyme) in the cell supernatant or extracellular space. As shown herein, bacterial strains can provide or produce or release such a 5'-nucleotidase enzyme (or ecto 5'-nucleotidase enzyme) into the cell supernatant or extracellular space where it can then convert appropriate substrate to adenosine. Appropriate substrates include AMP.

Thus, when bacterial strains are referred to herein as being capable of producing adenosine, this includes the direct production of adenosine by the bacterial cells themselves and also includes the production of adenosine by the bacterial cells by way of the cells having an active 5'-nucleotidase enzyme (for example present on the bacterial cell surface or released into the cell supernatant or extracellular space) and thereby converting or being able to convert appropriate substrate, e.g. AMP, to adenosine. Such substrate can be naturally present, e.g. endogenously in the environment, or can be provided to the bacteria, e.g. by exogenous means.

Such strains can thus result in increased levels of melatonin, for example in comparison with the levels where no such strains are present.

Melatonin is known to be produced in the GI tract and thus production or increased production in this region should be physiologically effective. Preferably, the amount of melatonin produced is clinically or therapeutically significant. Thus, the strains of the invention can be used to treat any disease or condition associated with (or characterised by) reduced or decreased levels of melatonin, or associated with (or characterised by) melatonin deficiency, or can be used to treat any disease or condition which would benefit from increased levels of melatonin. Such diseases or conditions (and indeed subjects suffering from such diseases or conditions) would be readily recognised by those skilled in the art and would for example include diseases, conditions or subjects which have low, reduced e.g. significantly reduced (or abnormal) levels of melatonin or melatonin deficiency, e.g. compared to levels in a normal or healthy subject, for example levels in a normal or healthy subject of the same, equivalent or comparable age. A preferred example of such a disease is infantile colic. Preferred strains for such therapeutic uses are those which produce melatonin or adenosine.

Thus, yet further aspects of the invention provide a lactic acid bacterial strain which is capable of producing or inducing the production of melatonin, for example by virtue of said strain being capable of producing or inducing the production of adenosine, or a lactic acid bacterial strain which is capable of producing or inducing the production of adenosine. Therapeutic uses of such strains are also provided. Preferably, said strains have a gene encoding a 5'-nucleotidase or such strains have an active 5'-nucleotidase enzyme, for example to convert AMP (or other appropriate substrate) to adenosine. Exemplary levels of adenosine production or levels of 5'-nucleotidase activity or melatonin production are described elsewhere herein.

Preferred strains of the present invention are *L. reuteri* strains, more preferably *L. reuteri* strains DSM 32846, DSM 32847, DSM 32848, DSM 32849 and/or DSM 33198 (the depositary details of which are provided elsewhere herein), and such strains, e.g. isolated strains or biologically pure cultures or preparations of such strains, form further aspects of the invention, as do compositions (e.g. pharmaceutical or nutritional, e.g. food supplements, or probiotic, compositions, e.g. with pharmaceutically or nutritionally acceptable diluents and/or excipients) comprising said strains, or the therapeutic use of such strains, for example as described elsewhere herein, in particular for the treatment or prevention of infantile colic (or other diseases as described elsewhere herein). In some embodiments the DSM 17938 strain is not used. Thus, the present invention provides the *Lactobacillus reuteri* strains DSM 32846, DSM 32847, DSM 32848, DSM 32849 and/or DSM 33198 for use in therapy, for example for the treatment or prevention of diseases as described elsewhere herein. The present invention further provides the *Lactobacillus reuteri* strains DSM 32846, DSM 32847, DSM 32848, DSM 32849 and/or DSM33198 for use in the treatment or prevention of infantile colic.

Thus, a yet further aspect of the invention provides a method of treatment or prevention of infantile colic, or other diseases as described elsewhere herein, in a subject, said method comprising the step of administering an effective amount of the *Lactobacillus reuteri* strain DSM 32846, DSM 32847, DSM 32848, DSM 32849 and/or DSM 33198, to said subject.

In another aspect, the present invention provides the use of the *Lactobacillus reuteri* strains DSM 32846, DSM 32847, DSM 32848, DSM 32849 and/or DSM 33198 in the manufacture of a medicament or composition for use in the treatment or prevention of infantile colic, or other disease as described elsewhere herein, in a subject.

Alternative and preferred embodiments and features of the invention as described elsewhere herein apply equally to the methods of treatment and uses of the invention described here and elsewhere herein.

Figure 5:
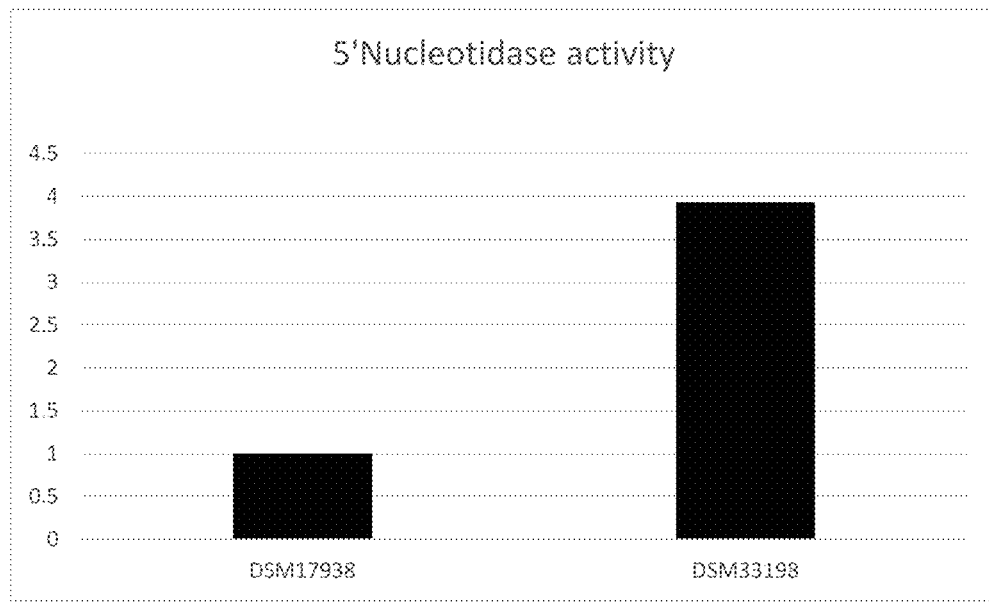
FIG. 5A shows the measurement of 5'-nucleotidase activity in the supernatant of *L. reuteri* DSM 33198 bacterial cells as compared to DSM 17938 bacterial cells.
FIG. 5B shows the measurement of 5'-nucleotidase activity in the supernatant of various *L. reuteri* bacterial cells as compared to DSM 17938 bacterial cells.
Figure 5:
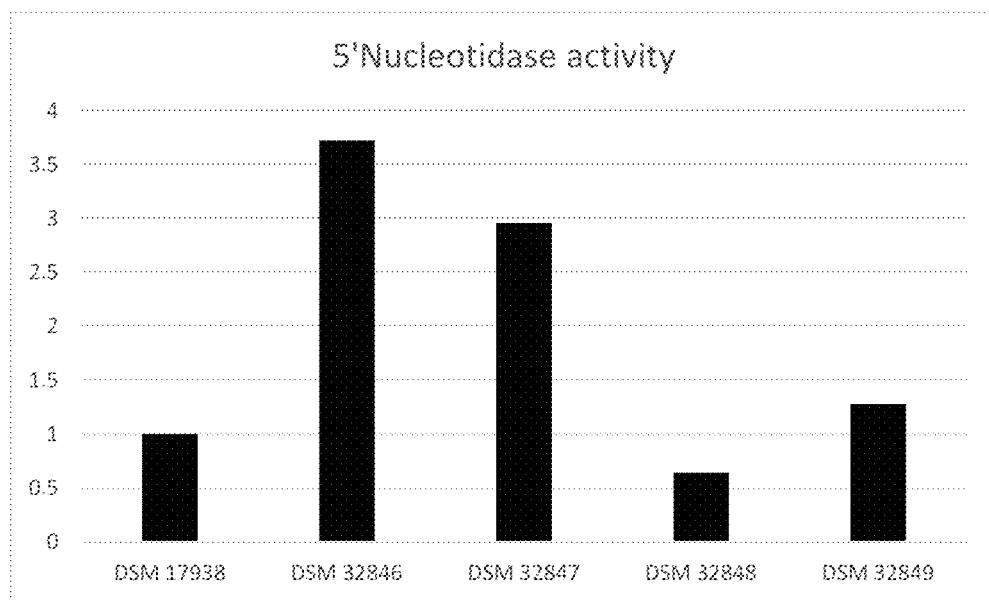

The strains *L. reuteri* DSM 32846, DSM 32847, DSM 32848, DSM 32849 and/or DSM 33198 have been selected for their capability to produce adenosine, for example by having a gene encoding a 5'-nucleotidase, and an active 5'-nucleotidase enzyme which can convert AMP substrate to adenosine, and are suitable not only to increase levels of adenosine (e.g. in comparison to levels where the strains are not present) but also to increase levels of melatonin, for example by increasing levels of AANAT as described elsewhere herein. The strains comprise an active cell wall anchored 5'-nucleotidase enzyme and also show 5'-nucleotidase enzyme activity in their respective supernatants (see FIG. 3 and FIG. 5 A/B).

These strains of *L. reuteri* have been developed (in other words are modified or adapted or evolved) from naturally occurring strains and have also been selected for one or more other improved properties such as increased resistance to bile or increased adherence to mucosal surfaces, e.g. surfaces of the GI tract. Thus, DSM 32846 and DSM 32847 have been evolved to be more tolerant to bile acids and thereby for example survive in larger numbers in the GI-tract. DSM 32848 and DSM 32849 have been evolved to adhere better to mucus, with the aim to colonize better in the GI-tract and thereby function better for example according to the present invention. The *L. reuteri* strain DSM 33198 has also been modified in a multi-step selection process including a repeated freeze-drying procedure to allow it to be more tolerant and give a higher survival in the production process than its native isolate (parent strain). Thus, such strains do not correspond to strains occurring in nature and have been forced to evolve and are non-native strains. All strains *Lactobacillus reuteri* DSM 32846, DSM 32847, DSM 32848, DSM 32849 and DSM 33198 are selected.

Preferred strains are DSM 32846, DSM 32847, DSM 32849 or DSM 33198. More preferred strains are DSM 32846, DSM 32847 or DSM 33198.

In one embodiment strains *Lactobacillus reuteri* DSM 32846, DSM 32847, DSM 32848 and/or DSM 32849 are selected or used. Preferred strains are DSM 32846, DSM 32847 or DSM 32849. More preferred strains are DSM 32846 or DSM 32847, for example DSM 32846 is preferred in some embodiments. In some embodiments, strain DSM 33198 is selected or used.

The present invention provides the use of a bacterial strain, e.g. a lactic acid bacterial strain, which is capable of producing or inducing the production of adenosine (e.g. increasing levels of adenosine, or increasing or promoting the production of adenosine), in the manufacture of a medicament or composition for use in the production of adenosine in a subject.

Such methods and uses can be used in the treatment or prevention of infantile colic or other diseases as described elsewhere herein, for example irritable bowel syndrome (IBS), sleep disorders, or neurodegenerative diseases or disorders, for example Alzheimer's disease or other types of dementia, for example other types of senile dementia. Such diseases are also examples of diseases associated with (or characterised by) a deficiency or reduction in melatonin, or which would for example benefit from elevated or increased levels of melatonin.

Gastrointestinal motility means the stretching and contractions of the muscles in the gastrointestinal tract to transfer foods being digested. The synchronized contraction of these muscles is called peristalsis.

There are a great number of locally released factors including hormones in the gastrointestinal tract that modulate motility and secretion. The movements of the digestive system, and the transit of the contents within it define the motility. When nerves and/or muscles in any portion of the digestive tract, the gastrointestinal motor function, do not function with normal strength and coordination, a person develops symptoms related to motility disturbances.

It has been described that disturbances of motor function produce a variety of symptoms in various gut regions such as in a subject with infantile colic.

Infantile colic is the term used to describe infants who cry excessively for no apparent reason during the first three months of life. Colic is one of the most distressing problems of infancy. It is distressing for the infant, the parents, and for the health care provider. The cause of colic is not fully understood.

New-borns hormone immaturity is implicated to be a major factor in early problems of the development of gut motility and thereby also causing pain and crying of the infant, such as in infantile colic.

Melatonin is a hormone that has the ability to support biological rhythms and has important effects on many functions in humans and animals. The hormone influences gastrointestinal motility by selective receptors (melatonin receptors) expressed on the smooth muscles and myenteric plexus cells of the gastrointestinal tract. The basic mechanism underlying the gastrointestinal smooth muscle contraction is the cyclic generation of electrical current. The myoelectric activity of gastrointestinal tract consists of two kinds of electrical potentials: slow wave and spike activity organized in the myoelectric migrating complex.

A precursor to melatonin is serotonin, a neurotransmitter itself that can be derived from the amino acid tryptophan.

It has been shown that serotonin induced decrease of the food transit is in part blocked by melatonin. It is a counter-balancing system of melatonin and serotonin in regulation of gut activity.

Further the functional and balanced melatonin-serotonin system affect appetite and digestive processes by endocrine as well as paracrine effects in both the brain and the GI tract.

The action of the two hormones seems to have the contrary effect on the motility and the end effects are dose dependent. Melatonin and serotonin are also known to be involved in the hypersensitivity processes and pain conduction.

Melatonin, also known as N-acetyl-5-methoxy tryptamine, is a hormone and a neurotransmitter earlier thought to be secreted predominantly by the pineal gland. But there are important extra-pineal sites of melatonin production, such as the retina and the gastrointestinal tract. There are now reports showing at least 400 times more melatonin in the gastrointestinal tract than in the pineal gland. Circadian variation of gastrointestinal melatonin does not appear to be controlled by light exposure (like the pineal gland), but by eating and food composition.

Synchronization between production and the different circadian rhythms and the following release of serotonin and melatonin in young infants is important to avoid gut motility disturbances and pain, such as infantile colic (IC).

Serotonin increases intestinal smooth muscle contraction, and melatonin relaxes intestinal smooth muscles. The serotonin concentration peaks can cause intestinal cramps if not balanced by other agents, whereof melatonin is an important one. Both serotonin and melatonin have circadian rhythms. While there is serotonin produced and serotonin circadian rhythms developed when an infant is born, the endogenous melatonin production and melatonin circadian rhythm is in many infants not ready to begin until after the $3^{rd}$ month in life. This time coincides with the time of normal disappearance of infantile colic. It has been shown that melatonin is low in the mornings early in life for the infants who have colic, whereas it is high in infant who does not have colic (Cengiz et al 2015, Turkish journal of family medicine and primary care; 9 (1)/10-15). Such infants (for example infants with forms of infantile colic associated with deficiencies in melatonin or melatonin balance, for example deficiencies in melatonin levels in the mornings, for example at or before 6 AM, 8 AM, 10 AM or 12 noon) are examples of subjects which can be treated using the present invention.

Thus, although some children appear able to produce and release needed melatonin endogenously, from their food and/or their intestinal bacteria and are therefore less likely to develop infantile colic, there are many others who do not, and thus need added support to prevent or treat IC. Such infants (for example infants with deficiencies in melatonin caused for example by a not fully developed intestinal microbiome or infants suffering from nutrition problems or feeding problems) are also examples of subjects which can be treated using the present invention.

It can be said that infantile colic is a condition of melatonin-deficiency. This is especially important for children in stressful situations, or who are less able to cope with stress, such as for children born before full gestational time or not fully functional food metabolism etc. Such infants (for example infants with deficiencies in melatonin born before full gestational time, or by cesarean section, or without fully functional food metabolism) are also examples of subjects which can be treated using the present invention.

Another example of a condition that relates to a balance of melatonin function is irritable bowel syndrome (IBS) which is a common disorder characterized by recurrent abdominal pain or discomfort, in combination with disturbed bowel habits in the absence of identifiable causes. Melatonin is suggested to show a positive effect on pain perception and bowel habits (Siah K T H et al, 2014, World J Gastroenterol; 20(10): 2492-2498). Thus, subjects having IBS, in particular forms of IBS associated with deficiencies in melatonin or melatonin balance, are also examples of subjects which can be treated using the present invention.

Melatonin deficiency has been mainly investigated in the pineal gland, circulation, saliva, cerebrospinal fluid, and, by measuring the metabolite 6-sulfatoxymelatonin, in urine.

There are more than 20 types of enteroendocrine cells in the intestine, which makes it the largest endocrine organ in the human body. Enterochromaffin (EC) cells are a type of enteroendocrine and neuroendocrine cell. They reside alongside the epithelium lining the lumen of the digestive tract and play a crucial role in gastrointestinal regulation, particularly intestinal motility and secretion. EC cells modulate neuron signalling in the enteric nervous system (ENS) via the secretion of the neurotransmitter serotonin and other peptides, they further express adenosine receptors and have an active synthesis of melatonin.

A common symptom of insufficient melatonin signalling is sleep disturbances and melatonin is one of the most popular natural health supplements of our time. Melatonin is often referred to as "the hormone of darkness" because its synthesis and secretion is in some locations of the body enhanced by darkness and inhibited by light. Sleep disturbances are highly prevalent in children and, without appropriate treatment, can become chronic and last for many years (Esposito et al. 2019, J Transl Med, 17:77). Even the elderly population is reported to experience sleep disturbances. The night-time melatonin peak is regularly observed to decrease during aging. Thus, subjects having or suffering from sleep disturbances or sleep disorders, in particular forms of sleep disturbances or sleep disorders associated with deficiencies in melatonin or melatonin balance, are also examples of subjects which can be treated using the present invention.

Decreased levels of melatonin have also been repeatedly described in neurodegenerative disorders, especially in Alzheimer's disease and other types of senile dementia (Blumenbach Johann Friedrich, 2012, The Scientific World Journal Volume 2012, Article ID 640389). Thus, subjects having such neurodegenerative disorders, in particular forms of such neurodegenerative disorders associated with deficiencies in melatonin or melatonin balance, are also examples of subjects which can be treated using the present invention.

Figure 1:
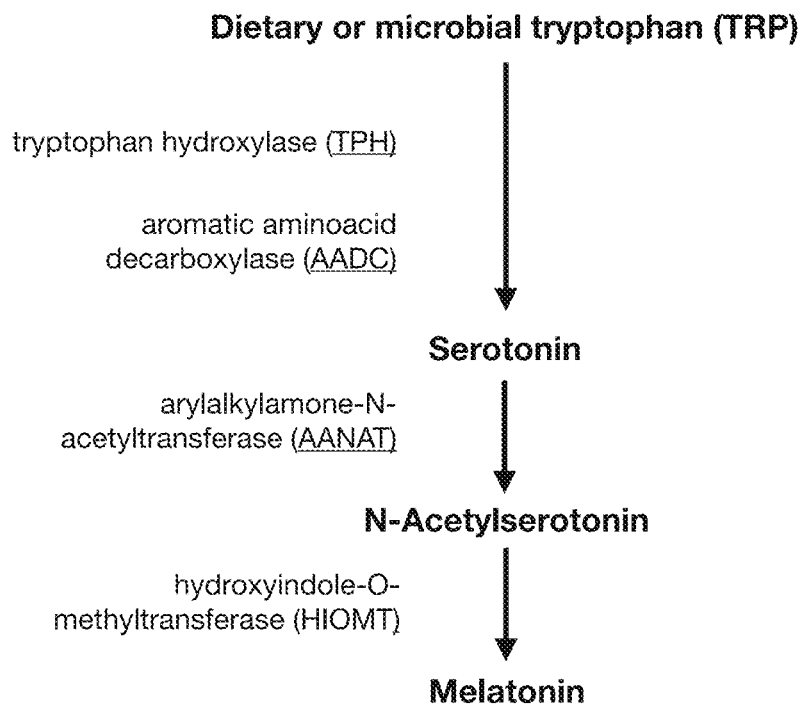
FIG. 1 is a schematic showing the melatonin production pathway.

The rate of melatonin formation depends on the activity of the enzyme arylalkylamine-N-acetyltransferase (AANAT) (FIG. 1 and FIG. 2) in the pineal gland but also at the extra-pineal sites of melatonin production, such as in the gastrointestinal tract.

Adenosine increases intracellular cAMP levels via adenosine receptor, which increases the production of AANAT, the rate limiting enzyme in melatonin synthesis.

It is an object of the present invention to use adenosine producing lactic acid strains to prevent and/or treat infantile colic.

It is another object of the present invention to use adenosine producing lactic acid strains to prevent and/or treat IBS.

It is another object of the present invention to use adenosine producing lactic acid strains to prevent and/or treat sleep disorders.

It is another object of the present invention to use adenosine producing lactic acid strains to prevent and/or treat neurodegenerative disorders, e.g. Alzheimer's disease and other types of dementia, e.g. other types of senile dementia.

This invention also relates to a method for the selection of specific bacterial strains, including lactic acid bacterial strains, capable of producing adenosine and the use of such strains to deliver beneficial effects for an infant having colic or being at risk for colic. It is a further object of the invention to provide new bacterial strains, which are capable of producing adenosine.

One important metabolic process in the human body is purine metabolism, wherein purines are metabolized and broken down by specific enzymes. One example of those enzymes are ecto-5'-nucleotidase (CD73), which is considered to be a key enzyme in the generation of adenosine.

The inventors surprisingly found that some specific probiotic bacterial strains were capable of producing adenosine.

The present invention thus includes a new method of selecting specific bacterial strains, including strains of lactic acid bacteria, that are effective in producing adenosine. The purpose of selecting specific bacterial strains is to use them for treating certain disorders such as infantile colic (or other diseases as described elsewhere herein).

The present invention provides a method for selecting bacterial strains, in particular lactic acid bacterial strains, which are useful as probiotics and in therapy, e.g. as pharmaceuticals or as food supplements.

One aspect of the present invention thus provides a method for the selection of a bacterial strain, preferably a lactic acid bacterial strain, capable of producing adenosine, wherein said method comprises:
  a) screening a bacterial strain, e.g. a lactic acid bacterial strain, for the presence of a gene encoding a 5'-nucleotidase, e.g. a cell wall anchored 5'-nucleotidase; and/or
  b) screening a bacterial strain, e.g. a lactic acid bacterial strain, or its supernatant for the presence of an active 5'-nucleotidase enzyme, e.g. a cell wall anchored 5'-nucleotidase enzyme.

Such 5'-nucleotidase (5'NT) enzymes can also be referred to as ecto-5' nucleotidase enzymes or CD73 (cluster of differentiation 73). Strains which are capable of producing adenosine can then be selected.

Viewed alternatively, the present invention provides a method for the selection of a bacterial strain, preferably a lactic acid bacterial strain, by screening a bacterial strain, e.g. a lactic acid bacterial strain, for its capability to produce adenosine and selecting a strain which has that capability.

Once an appropriate strain has been selected using the method of the present invention it can then be used for the production, e.g. the local production, of adenosine in a subject.

A bacterial strain, e.g. a lactic acid bacterial strain, selected, produced, obtained or obtainable by the methods of the invention, wherein said strain is capable of producing adenosine, for example local production of adenosine in a subject, is a yet further aspect of the invention.

Therapeutic uses in infantile colic (or other diseases as described elsewhere herein) of the strains selected by the present invention are also provided.

Thus, a further aspect of the present invention provides a bacterial strain, e.g. a lactic acid bacterial strain, selected, produced, obtained or obtainable by the method of the invention, wherein said strain has a 5'-nucleotidase gene or an active 5'-nucleotidase enzyme and is capable of producing adenosine, for use in the production, e.g. local production, of adenosine in a subject.

Alternative embodiments of the invention provide a bacterial strain, e.g. a lactic acid bacterial strain, wherein said strain has a 5'-nucleotidase gene or an active 5'-nucleotidase enzyme and is capable of producing adenosine, for use in the production, e.g. local production, of adenosine in a subject. Preferred features of this strain and its uses are described elsewhere herein.

As will be outlined elsewhere herein, a particular embodiment of the invention is the prevention and/or treatment of infantile colic (or other diseases as described elsewhere herein).

Methods of treatment or methods for the production, e.g. local production, of adenosine in a subject, are also provided, said methods comprising the administration of a bacterial strain, e.g. a lactic acid bacterial strain, selected, produced, obtained or obtainable by the selection method of the invention, or the administration of a bacterial strain, e.g. a lactic acid bacterial strain, wherein said strain has a 5'nucleotidase gene or an active 5'nucleotidase enzyme and is capable of producing adenosine, to said subject in an amount effective to enable production, e.g. local production, of adenosine in said subject. Preferred features of the strain and its therapeutic uses, e.g. in infantile colic (or other diseases as described elsewhere herein), are described elsewhere herein.

Also provided by the present invention is the use of a bacterial strain, e.g. a lactic acid bacterial strain, selected, produced, obtained or obtainable by the selection method of the invention, wherein said strain has a 5'nucleotidase gene or an active 5'nucleotidase enzyme and is capable of producing adenosine, in the manufacture of a composition or medicament for use in the production, e.g. local production, of adenosine in a subject. Alternative embodiments provide the use of a bacterial strain, e.g. a lactic acid bacterial strain, wherein said strain has a 5'nucleotidase gene or an active 5'nucleotidase enzyme and is capable of producing adenosine, in the manufacture of a composition or medicament for use in the production, e.g. local production, of adenosine in a subject. Preferred features of the strain and its therapeutic uses, e.g. in infantile colic (or other diseases as described elsewhere herein), are described elsewhere herein.

Products or compositions, e.g. pharmaceutical compositions, probiotic compositions, or dietary/nutraceutical compositions, comprising the bacterial strains (for example comprising one or more of the bacterial strains) as described herein (e.g. bacterial strains capable of producing or inducing adenosine, melatonin, etc.) and uses of said products or compositions in methods and uses as described herein form yet further aspects of the invention.

The Food and Agricultural Organization of the United Nations define probiotics as "live microorganisms which when administered in adequate amounts confer a health benefit on the host". Nowadays, a number of different bacteria are used as probiotics for example, lactic-acid producing bacteria such as strains of *Lactobacillus* and *Bifidobacterium*.

Alternative and preferred embodiments and features of the invention as described elsewhere herein apply equally to the methods of treatment, uses and products of the invention.

As described above, the present invention relates to the selection and use of bacterial strains that are capable of producing adenosine.

Said strains which are effective in producing adenosine can be used for local production of adenosine in a subject, e.g. a mammal, preferably a human.

Thus, as outlined above, the present invention provides various methods for the selection or screening of bacterial strains capable of producing adenosine.

Some of the methods comprise a step (e.g. step a)) of screening for the presence of a gene encoding a 5'-nucleotidase, e.g. a cell wall anchored 5'-nucleotidase. Such screening can be carried out using any appropriate method and strains positive for a 5'-nucleotidase gene are selected. Such methods will conveniently be carried out in vitro, for example will be genetic or nucleic-acid based methods to detect the presence of a gene encoding a 5'nucleotidase, e.g. a cell wall anchored 5'nucleotidase (or an identificatory fragment thereof) the sequences of which are known in the art. For example, a PCR protocol (or other nucleic acid based technique) can be readily designed to do this based on the known nucleic acid sequences encoding the enzymes, or as an alternative, genome sequences of candidate strains could be scrutinized with the aim to identify the said gene encoding a 5'nucleotidase, e.g. a cell wall anchored 5'nucleotidase, for example, based on homology to known 5'nucleotidase sequences, including for example the presence of an LPXTG-motif (SEQ ID NO:1) as discussed below.

An exemplary gene to be detected in the methods of the invention is the cell wall anchored (ecto) 5'nucleotidase gene from *L. reuteri* (e.g. GenBank accession number: AEI56270.1, LPXTG-motif cell wall anchor domain protein [*Lactobacillus reuteri* SD2112]), or an appropriate homologue/5' nucleotidase from other species of bacteria, e.g. other lactic acid bacteria. An exemplary technique is described in the experimental Examples.

Some methods comprise a step (e.g. step b)) of screening for the presence of an active (functional) 5'-nucleotidase enzyme, e.g. a cell wall anchored 5'nucleotidase enzyme. Such a step can be carried out using any appropriate method, for example, using an enzymatic assay. The 5'-nucleotidase enzyme catalyzes the following reaction: AMP+ $H_2O \leftrightarrows$ adenosine+phosphate (AMP is adenosine monophosphate) and an assay to measure this reaction can readily be used to determine the presence of an active 5'-nucleotidase enzyme (or 5'-nucleotidase activity). In other words the reference herein to an active or functional 5'-nucleotidase enzyme is one which is capable of catalyzing this reaction under suitable conditions, e.g. when supplied with appropriate substrate such as AMP. The activity of the 5'-nucleotidase enzyme can, if desired, be quantified, e.g. in such an enzymatic assay, for example by measuring the amount or concentration of phosphate or adenosine or other appropriate downstream product of adenosine which is generated in the reaction and can be measured or quantitated. The activity can conveniently be measured on a sample of the bacterial cells, or the supernatant from the bacterial cells.

Methods for carrying out such an assay would be well-known to a person skilled in the art. For example, appropriate kits are commercially available, such as the Crystal Chem 5'-Nucleotidase Assay Kit (Crystal Chem, catalogue #80229, Downers Grove, IL, USA) in which 5'-nucleotidase enzyme activity is measured by way of the production of a dye (a quinone dye) which is formed as a downstream product of the conversion of AMP to adenosine (i.e. as a result of the production of adenosine). AMP is provided as a substrate. An exemplary technique is described in the Examples section. Appropriate methodology is also readily available from other reagent suppliers, e.g. Sigma, in conjunction with their 5'-nucleotidase enzyme reagent.

Strains with high or significant production levels of 5'-nucleotidase enzyme (or 5'-nucleotidase activity) are preferred, for example strains that have a 5'-nucleotidase activity of at least or greater than 2 units/L (units per litre) and/or are capable of producing adenosine at a level of at least or greater than 2 $\mu$mol L$^{-1}$ min$^{-1}$ ($\mu$mol per litre per minute). Thus, in preferred embodiments, a strain is selected for having 5'-nucleotidase activity at a level of at least, or greater than, 3, 4, 5, 8, 9, 10, 15, 20, 25, 30, 35, 40, 45, 50, 60, 70, 80, 90, 100, 110, 120, 130, 140 or 150 units/L, and/or is capable of producing adenosine at a level of at least, or greater than, 3, 4, 5, 8, 9, 10, 15, 20, 25, 30, 35, 40, 45, 50, 60, 70, 80, 90, 100, 110, 120, 130, 140 or 150 $\mu$mol L$^{-1}$ min$^{-1}$. In some embodiments such values can represent upper limits. Such values generally refer to values of 5'-nucleotidase activity measured on a sample of the bacterial cells, e.g. on the surface of the bacterial cells, or in the supernatant of the bacterial cells in culture, preferably in the supernatant. Such values generally refer to adenosine levels (preferably extracellular adenosine levels) measured in a sample of the bacterial cells, e.g. in the supernatant of the bacterial cells in culture. Such values generally refer to values of 5'-nucleotidase activity (or adenosine levels) when measured with a concentration of 10$^9$ bacteria/ml, or the supernatant from such a culture. One unit is defined as the amount of enzyme needed for producing 1 $\mu$mol product/min (e.g. 1 $\mu$mol product/litre/min). The concentration in units/liter will then correspond to the enzyme concentration needed for increasing the concentration with 1 $\mu$M/min (e.g. 1 $\mu$M/litre/min). An appropriate and exemplified assay for measuring this activity is shown in the Examples using the 5'-nucleotidase kit (#80229) from Crystal Chem Inc. Thus, in preferred embodiments the above units and values refer to units and values when measured using this kit and/or the conditions set out in the Examples, in particular with a concentration of 10$^9$ bacteria/ml, or the supernatant from such a culture, or an equivalent assay. Thus, such methods will conveniently be carried out in vitro.

Methods comprising at least step b) will be preferred, as the presence of a gene encoding a 5'-nucleotidase is not always indicative of the presence of an active 5'-nucleotidase enzyme. In the methods, uses and lactic acid bacteria of the invention, adenosine production or adenosine activity should take place extracellularly, i.e. outside or on the surface of the lactic acid bacteria, so that it can for example be present in the supernatant or other extracellular fluid produced by the lactic acid bacteria. Thus, the presence of an active 5'-nucleotidase enzyme on the cell surface, for example in the form of a cell wall anchored 5'-nucleotidase, or extracellular from the bacterial cell, for example in the supernatant, can be a useful feature such that the reaction to produce adenosine takes place outside the cell, for example on the surface of the bacterial cell.

Thus, the production of good levels of adenosine (e.g. extracellular adenosine produced by the 5'-nucleotidase enzyme) can also be an indicator of the presence of a 5'-nucleotidase gene or the presence of an active 5'-nucleotidase enzyme. Thus, the selection method of the invention can also involve the step of selecting a strain which is producing adenosine. Strains with high or significant production levels of adenosine, e.g. extracellular adenosine, are preferred, for example strains that produce adenosine at a level which is therapeutically effective in a subject, or at a level such that increased (and preferably therapeutically effective) levels of melatonin are observed. Such values generally refer to values of adenosine measured in the supernatant of strains in culture or on the cell surface of strains in culture (in vitro) and some exemplary specific values are provided above.

However, in some embodiments it is appropriate to refer to values, levels or amounts of adenosine produced in a subject, for example locally, e.g. at the site of administration, e.g. in the gastrointestinal tract. For example, preferred strains can enable increased production of adenosine, for example increased in vivo production, e.g. local production (e.g. in the GI tract), of adenosine, for example when compared to a relevant control as described elsewhere herein, such as the levels of adenosine when no strains are administered, or the base or natural level of adenosine in a particular subject.

In all aspects of the invention described herein, local production can refer to production or levels of adenosine at the site of administration, for example production or levels of adenosine in the gastrointestinal tract (e.g. when administration is oral). In one aspect the local production of adenosine can have systemic downstream effects and may increase levels of adenosine or melatonin in the circulatory system, for example in blood or plasma, or other places outside the gastrointestinal tract.

Strains which can give rise to increased local levels of adenosine (or melatonin or 5'nucleotidase activity), for example in the GI tract of a subject, are thus preferred, in particular where such an effect is observed when the strains are administered orally. Preferably said increases are measurable or significant increases, for example are statistically or clinically significant. By way of example, strains which can give rise to increases of at least, or up to, 1.5 fold, 2 fold, 2.5 fold, 3 fold, 3.5 fold, 4 fold, 4.5 fold, 5 fold, 6 fold, 7 fold, 8 fold, 9 fold or 10 fold, in levels of adenosine (or melatonin or 5'nucleotidase activity), for example local levels of adenosine (or melatonin or 5'nucleotidase activity), are preferred. Any appropriate comparison can be used, for example an increase when compared to the levels observed when no strain is administered, or the levels when a control formulation, e.g. a control formulation not containing the relevant strain, is administered.

Appropriate methods of measuring levels of adenosine (or melatonin or 5'nucleotidase activity) production would be well known to a person skilled in the art. Thus, in some embodiments of the invention, the selection method will involve the step of detecting or determining the amount or level (e.g. the concentration) of adenosine produced by a candidate strain.

Optionally, the levels of adenosine production or 5'nucleotidase activity (or indeed any other appropriate property of the strains described herein) can conveniently be compared to positive or negative control strains. An appropriate positive control strain might be DSM 17938 which has been shown in the Examples to produce significant levels of adenosine/5'nucleotidase activity, for example in the supernatant of bacterial cells. Some strains will produce higher levels, sometimes significantly higher levels, of adenosine/5'nucleotidase activity than DSM 17938, for example in the supernatant of bacterial cells. Thus, strains capable of producing higher (increased) levels, or significantly higher (increased) levels, of 5'nucleotidase activity than DSM 17938, for example in the supernatant of bacterial cells, for example when assessed in vitro, form a yet further aspect of the invention. Exemplary strains are DSM 32846, DSM 32847, DSM 32849 and DSM 33198 (see FIG. 3 and FIG. 5 A/B). Viewed alternatively, strains capable of producing or inducing production of higher (increased) levels, or significantly higher (increased) levels, of adenosine than DSM 17938, for example in the supernatant of bacterial cells, for example when assessed in vitro, form a yet further aspect of the invention. For example, strains capable of producing or inducing production of higher (increased) levels, or significantly higher (increased) levels of adenosine in a subject, for example higher etc., local levels of adenosine in a subject than DSM 17938, for example when assessed in vivo, form a yet further aspect of the invention, in particular where such an effect is observed when the strains are administered orally.

In general, strains which have one or more improved (e.g. significantly improved) properties when compared to DSM17938 are preferred for some embodiments.

Preferably said increases (in adenosine production or 5'nucleotidase activity) are measurable or significant increases, for example are statistically or clinically significant. By way of example, strains which can give rise to increases of at least, or up to 10%, 20%, 30%, 40%, 50%, 60%, 70%, 80%, 90%, 100%, 150%, 200%, 250%, 300%, 350%, 400%, 450%, 500%, 550%, or higher, in levels of adenosine, for example local or in vitro levels of adenosine, or in levels of 5'nucleotidase activity (for example when assessed in vitro), compared to the levels with DSM 17938 are preferred. Viewed alternatively, strains which can give rise to increases of at least, or up to, 1.5 fold, 2 fold, 2.5 fold, 3 fold, 3.5 fold, 4 fold, 4.5 fold, 5 fold, 6 fold, 7 fold, 8 fold, 9 fold, or 10 fold, in levels of adenosine, for example local or in vitro levels of adenosine, or in levels of 5'nucleotidase activity, compared to the levels with DSM 17938 are preferred. In vitro levels can conveniently be measured as described elsewhere herein, for example in bacterial cultures. Preferably, such increases are increases in extracellular levels of adenosine or 5'nucleotidase activity, for example as measured in vitro, for example in the supernatant of bacterial cultures.

An appropriate negative control strain might be a strain that does not contain a gene encoding a 5'nucleotidase or does not contain an active 5'nucleotidase enzyme (or does not have 5'nucleotidase activity as described elsewhere herein).

Because of the downstream uses of the strains which are selected by the methods of the invention, after adenosine producing strains are selected or isolated, other embodiments will involve the further steps of culturing or propagating or producing such strains, and optionally formulating said cultured or propagated or produced strains into a composition comprising said strain, e.g. a pharmaceutical or nutritional composition, e.g. as described elsewhere herein, or possibly storing such strains for future uses, for example through lyophilisation or freeze drying. In one embodiment the bacterial strains are provided in a freeze-dried form.

The selection steps of the methods of the invention (and indeed the therapeutic methods as described herein) will generally need to be carried out in an appropriate culture medium (or in vivo environment), which supports adenosine production. Preferred culture media (or in vivo environment) will contain an appropriate carbon source, which will support the production of adenosine by said strain, preferably together with an appropriate substrate for adenosine production by the 5'nucleotidase enzyme, e.g. AMP.

Although such assays can conveniently be carried out in vitro, another option would be to assess the strains in an appropriate ex vivo assay, e.g. using an appropriate intestinal enteroid model (see for example the enteroid model and assays described in Example 5, where for example levels of melatonin can be assessed).

Thus, although any appropriate in vitro or ex vivo models for assessment of the strains, for example for assessment of the induction of adenosine or melatonin production by the strains, preferred in vitro or ex vivo models for assessment of the strains are intestinal enteroid models, preferably human intestinal enteroid models, which can for example be used to assess melatonin levels. Such models preferably comprise enteroendocrine cells, for example as described in Example 5.

Preferred strains of the invention are capable of producing or inducing the production of at least or up to 10, 20, 30, 40, 50, 60 or 70 pg/ml melatonin. In some embodiments such values can represent upper limits. Such values generally refer to levels of melatonin production induced by said strains when measured in an appropriate in vitro or ex vivo assay, for example refer to levels of melatonin produced by enteroendocrine cells (preferably human cells), or produced in an intestinal enteroid model comprising enteroendocrine cells (for example with % s of enteroendocrine cells as described elsewhere herein), preferably a model comprising human cells, when said cells are brought into contact with the strains of the invention or supernatant taken from said strains. An appropriate and exemplified assay for measuring this activity is shown in the Examples using a human intestinal enteroid model comprising enteroendocrine cells, e.g. at least 20% or 30%, for example 20-40%, 30-40% or up to 40%, enteroendocrine cells. Thus, in preferred embodiments the above values refer to values when measured using this assay (or an equivalent assay, for example with the above % s of enteroendocrine cells) and/or the conditions set out in the Examples.

Some strains will be capable of producing or inducing higher levels, sometimes significantly higher levels, of melatonin than DSM 17938, for example from enteroendocrine cells or in intestinal enteroid models as described above. Thus, strains capable of producing or inducing higher (increased) levels, or significantly higher (increased) levels, of melatonin than DSM 17938, for example when assessed as described above, e.g. using enteroendocrine cells or intestinal enteroid models, form a yet further aspect of the invention. Exemplary strains can give rise to increases of at least, or up to, 1.5 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold or 10 fold, in levels of melatonin production, compared to the levels with DSM 17938, and are preferred.

The screening methods of the invention can thus optionally comprise a further step of selecting a strain which is capable of producing or inducing the production of melatonin, for example using methodology as described above or any other appropriate methodology. Selected strains can preferably induce the production of melatonin at levels as described above.

In embodiments where more than one bacterial strain is screened using the methods of the invention, the amount of generated adenosine or 5'nucleotidase activity (or melatonin) can optionally be quantified and the bacterial strain, e.g. the lactic acid bacterial strain, with the highest activity or level of the 5'-nucleotidase enzyme, or a sufficiently high activity or level of the 5'-nucleotidase enzyme, for example with activities or levels as described elsewhere herein, for example with activities or levels higher (preferably significantly higher) than DSM17938, or the strain which produces the highest amount or level of adenosine or melatonin, or a sufficiently high amount or level of adenosine or melatonin, for example with amounts or levels as described elsewhere herein, for example with amounts or levels higher (preferably significantly higher) than DSM17938 can be selected.

It is thus a yet further aspect of the invention to provide a method for the selection of bacterial strains, preferably lactic acid bacterial strains, effective in producing adenosine (or melatonin) comprising:

a) screening lactic acid bacterial strains for the presence of a gene encoding a 5'-nucleotidase, e.g. a cell surface anchored 5'nucleotidase, and;
b) quantifying the activity of the 5'-nucleotidase enzyme and; optionally
c) selecting the lactic acid bacterial strain which has the highest or sufficiently high activity of the 5'-nucleotidase enzyme.

Methods comprising certain steps as described herein also include, where appropriate, methods consisting of these steps.

As set out above, a bacterial strain, e.g. a lactic acid bacterial strain, selected, produced, obtained or obtainable by the methods of the invention, wherein said strain is capable of producing adenosine, and preferably in turn producing or supporting production, e.g. increased production, of melatonin, is a yet further aspect of the invention.

Any appropriate bacterial strain, e.g. probiotic bacterial strain, for example any probiotic bacteria, can be subjected to the selection methods of the invention and any appropriate bacterial strain, e.g. probiotic bacterial strain, which is capable of producing adenosine can be used in the methods or uses of the present invention, e.g. in the therapeutic methods or uses described herein.

Preferred bacterial strains are lactic acid bacteria, for example *Lactobacillus* or *Bifidobacterium*. Particularly preferred bacterial strains are *Lactobacillus reuteri*, in particular the strains *Lactobacillus reuteri* DSM 32846, DSM 32847, DSM 32848 and DSM 32849 that were deposited under the Budapest Treaty at the DSMZ-Deutsche Sammlung von Mikroorganismen und Zellkulturen GmbH (Mascheroder Weg 1b, Inhoffenstr. 7B, D-38124 Braunschweig) on Jul. 4, 2018 and *Lactobacillus reuteri* DSM 33198 that was deposited under the Budapest Treaty at the DSMZ-Deutsche Sammlung von Mikroorganismen und Zellkulturen GmbH (Mascheroder Weg 1b, Inhoffenstr. 7B, D-38124 Braunschweig) on Jul. 9, 2019. These bacterial strains or isolated bacterial strains (and other strains, e.g. *L. reuteri* strains, in particular related *L. reuteri* strains, with one or more of the characteristics, e.g. the ability to produce or induce the effects on the production of adenosine and/or 5' nucleotidase activity, and/or melatonin, of one or more of these deposited strains) form preferred aspects of the invention and can for example be used to treat the diseases or conditions as described elsewhere herein or for any other uses as described herein. In some embodiments, the *L. reuteri* strain DSM 17938 is not used.

Thus, a yet further aspect of the invention provides the use of such strains to treat or prevent one or more of the diseases as described herein.

It is another object of the invention to provide a method for improving the use and effect of the treatment of the specific disorders as described herein comprising maximizing, increasing or improving the activity of the 5'-nucleotidase of the selected strains, e.g. lactic acid bacterial strains, which will preferably lead to increased or improved production of adenosine. This can be achieved by culturing the bacteria in specific growth conditions to allow a high yield of adenosine (or a higher, e.g. significantly higher, yield of adenosine, e.g. compared to the yield observed in the absence of the specific growth condition). In one embodiment of the invention, the specific growth condition can be e.g. culturing the lactic acid bacteria in normal growth medium supplemented with an appropriate substrate for adenosine production by the 5'nucleotidase enzyme, e.g. AMP, or appropriate upstream components of AMP such as ADP and/or ATP.

In a further related embodiment of the invention, to maximize the activity of the 5'-nucleotidase, a higher concentration of bacteria, e.g. lactic acid bacteria, can be administered. An exemplary concentration might be 2 to 10 times higher than a conventional dose.

In a further related embodiment of the invention, the 5'-nucleotidase gene can be overexpressed or induced in the bacterial strains by appropriate methods, e.g. the insertion of a plasmid vector with the 5'-nucleotidase gene under the control of an appropriate promoter, e.g. an inducible promoter. Alternatively, the 5'-nucleotidase gene could be overexpressed by inserting one or more additional copies of the gene into the bacterial cell, for example insertion on the chromosome of the bacterial cell, under the control of an appropriate promoter, e.g. an inducible or the native promoter.

As described above, the strains of the invention, or strains selected by, produced, obtained, or obtainable by the methods of the invention have uses in therapy. Thus, a further aspect of the invention provides the adenosine producing strains of the invention, or strains which are selected, obtained or obtainable using the selection methods of the invention, for use in the production, e.g. local production, of adenosine, and thereby preferably melatonin in a subject. In preferred embodiments of the invention, said production of adenosine, etc., and preferably melatonin is used for the treatment of infantile colic (and other diseases as described herein) which will benefit from production or increased production, e.g. local production, of adenosine and thereby melatonin.

The administration of the bacterial strains in the methods of treatment and uses of the invention is carried out in pharmaceutically, therapeutically, or physiologically effective amounts, to subjects (animals/mammals) in need of treatment. Thus, said methods and uses may involve the additional step of identifying a subject in need of treatment.

Treatment of disease or conditions in accordance with the present invention (for example treatment of pre-existing disease) includes cure of said disease or conditions, or any reduction or alleviation of disease (e.g. reduction in disease severity) or symptoms of disease.

The methods and uses of the present invention are suitable for prevention of diseases or conditions as well as treatment of diseases or conditions. Thus, prophylactic treatment is also encompassed by the invention. For this reason in the methods and uses of the present invention, treatment or therapy also includes prophylaxis or prevention where appropriate. Such preventative (or protective) aspects can conveniently be carried out on healthy or normal subjects as described herein, and can include both complete prevention and significant prevention. Similarly, significant prevention can include the scenario where severity of disease or symptoms of disease is reduced (e.g. measurably or significantly reduced) compared to the severity or symptoms which would be expected if no treatment is given.

A yet further aspect of the invention provides a strain or product for the therapeutic uses as defined elsewhere herein, wherein said use further comprises the administration of at least one further agent, e.g. a further therapeutic or nutritional agent. Exemplary agents might be substrate components which will increase or enhance the production of adenosine (e.g. a component which can increase or enhance the production of adenosine), or a source of such components.

Thus, in a yet further embodiment of the invention, where an adenosine producing bacteria is concerned, the administration of said strains or products further comprises the administration of a substrate component, e.g. AMP and/or a material or agent that produces this component. A preferred substrate would be AMP, or a source of AMP.

In such embodiments, the substrate component, or other additional component, could be added to the bacterial preparation directly before administration to the subject. Alternatively, it could be added to the bacterial preparation at the end of the manufacturing process, e.g. at the end of fermentation, after which the bacteria can be stored for future use, e.g. by lyophilisation or freeze-drying. Alternatively it can be administered separately as described below.

In such embodiments, the further therapeutic agent can be any further agent which is useful in the treatment of the disease in question.

Said further agents can be administered together with the strains or products of the invention (e.g. as a combined preparation) or can be administered separately. In addition, said further agents can be administered at the same time as the strains or products of the invention or at different time points, e.g. sequentially. Suitable administration regimes and timings can readily be determined by the skilled person depending on the further agent in question.

The present invention also provides a composition (or a combination product or kit) comprising:
 (i) a bacterial strain, e.g. a lactic acid bacterial strain, selected, produced, obtained or obtainable by the selection method of the invention (or a bacterial strain capable of producing or inducing adenosine production as otherwise defined herein), wherein said bacterial strain has a gene encoding a cell surface anchored 5'-nucleotidase or an active 5'nucleotidase enzyme and is capable of producing adenosine; and
 (ii) one or more substrate components or agents which will increase or enhance the production of adenosine, or a source of such components or agents.

Exemplary components or agents are outlined above. A preferred component is AMP or a source of AMP.

The invention also provides a composition (or a combination product or kit) suitable for increasing the production of melatonin or adenosine in a subject comprising:
 (i) a first bacterial strain, e.g. a lactic acid bacteria strain, capable of producing or inducing the production of melatonin or adenosine as described herein; and
 (ii) a further source of melatonin and/or adenosine, or one or more substrate components or agents to increase or enhance the production or induction of melatonin and/or adenosine, or a source of such components or agents, as appropriate, by the lactic acid bacteria strain.

A preferred component is AMP or a source of AMP.

In the kits or combination products of the invention, components (i) and (ii) are generally provided in separate compartments or vessels or as separate components of the kit or product. The kits may comprise further components, which may also be in separate compartment or vessels. Preferably the kits (or combination products) are for use in the methods or uses of the present invention as described herein, for example are for use in the treatment or prevention of other diseases described herein, in particular infantile colic. Instructions for use of the kits or products in the methods and uses of the invention may optionally be provided.

The term "subject" as used herein includes mammals, in particular humans, especially infants (for example where the disease to be prevented or treated is colic). In preferred embodiments of the invention, the selected strain, e.g. lactic acid bacterial strain, is administered to a human. For diseases other than colic, any subject, e.g. human subject, e.g.

adult or child or infant subject, suffering from said disease or suspected to be suffering from said disease or at risk from said disease is appropriate.

A preferred subject in accordance with the present invention is an infant of less than or up to 12 months old, preferably less than or up to 5 or 6 months old, preferably less than or up to 3 or 4 months old. Such subjects are particularly appropriate when the disease to be treated or prevented is infantile colic. Subjects can thus be treated from birth, or within the first few weeks (e.g. within the first 1, 2, 3 or 4 weeks) or within the first few months (e.g. within the first 1, 2, 3 or 4 months) of life.

As described elsewhere herein, preferred subjects are those suffering from infantile colic (or one of the other diseases as described herein) or believed or suspected to be suffering from infantile colic (or one of the other diseases as described herein). As the therapeutic uses of the invention can also be used to prevent disease, appropriate subjects include those at risk of suffering from infantile colic (or one of the other diseases as described herein).

Exemplary subjects will include exclusively (solely) breastfed infants and exclusively (solely) formula fed infants (non-breast fed infants) or infants which have been both breastfed and formula fed.

Other exemplary subjects include infants, in particular infants with colic, suspected of having colic, or at risk of developing colic, that do not yet produce or release melatonin or are otherwise unable to produce or release melatonin, for example infants in which the melatonin circadian cycle has not yet developed or started, or infants which are unable to produce or release the required melatonin from their food and/or their intestinal bacteria, or include infants which have low, reduced e.g. significantly reduced (or abnormal) levels of melatonin or melatonin deficiency, e.g. compared to levels in a normal or healthy subject, for example levels in a normal or healthy subject of the same, equivalent or comparable age.

For diseases other than colic, exemplary subjects include subjects which have low, reduced e.g. significantly reduced (or abnormal) levels of melatonin or melatonin deficiency, e.g. compared to levels in a normal or healthy subject, for example levels in a normal or healthy subject of the same, equivalent or comparable age.

Other exemplary subjects include infants that have some kind of nutritional or dietary issue or problem, for example which results in low or deficient levels of melatonin. Such subjects might include infants born before full gestational time, for example premature infants or infants born before 36 weeks of gestation, or infants that lack fully functional food metabolism, or infants which have problems feeding or nutrition problems.

Other exemplary subjects include those, preferably infants, with hormone immaturity (in other words suboptimal, subnormal, undeveloped, deficient, low or immature hormone production) for example compared to a normal infant or subject of the same age, for example melatonin immaturity, in particular those subjects which have deficiencies in gut motility as a result of said hormone immaturity. Such hormone immaturity, e.g. melatonin immaturity or melatonin reduction or deficiency, may for example be associated with some infants suffering with infantile colic. Other preferred diseases (and hence subjects) to be treated are diseases or conditions associated with melatonin deficiency (or subjects suffering from said diseases).

In all such subjects, if appropriate or necessary, levels of melatonin in said subject can readily be measured using techniques readily available and known in the art. For example, levels of melatonin can readily be measured in serum/blood or saliva samples. Commercial kits for such measurements are also available.

Any appropriate mode of administration can be used. Conveniently said administration is oral, rectal or by tube-feeding. Thus, the bacteria can be administered to the GI tract, or oral cavity, as desired or appropriate. The bacteria can be included in a baby formula or a food supplement or oil drops, as well as in a pharmaceutical formulation.

Appropriate doses of the strains, products and compositions of the invention as defined herein can readily be chosen depending on the disease (or condition) to be treated, the mode of administration and the formulation concerned.

For example, a dosage and administration regime is chosen such that the bacteria administered to the subject in accordance with the present invention can result in an increased production, e.g. local production, of adenosine (or melatonin) and to give rise to the desired therapeutic effects or health benefits in infantile colic (or other disease to be treated). Thus, preferably said dosage is a therapeutically effective dosage which is appropriate for the type of mammal and condition being treated and is for example administered to a subject in need thereof. For example, daily doses, e.g. a single daily dose, of $10^4$ to $10^{12}$, for example $10^5$ to $10^9$, or $10^6$ to $10^8$, or $10^8$ to $10^{10}$, or $10^{10}$ to $10^{12}$ total CFUs of bacteria may be used.

In one embodiment the daily dose (e.g. $10^5$ to $10^9$ or $10^6$ to $10^8$ or $10^8$ to $10^{10}$ or $10^{10}$ to $10^{12}$ of CFUs) is divided into several administrations e.g. 2-8 administrations (such as 3-5 administrations) or in association with every feeding (breast and/or formula) of the subject. In one embodiment, a higher dose, such as 2 to 10 or 10 to 100 times the dose after the starting period, and/or more frequently administered dose is administered as a starting dose for 3-14 days (e.g. 5-10 days, such as 7 days) for faster relief in a subject.

The term "increase" or "enhance" or "higher" (or equivalent terms) as described herein includes any measurable increase or elevation when compared with an appropriate control. Appropriate controls would readily be identified by a person skilled in the art and might include levels when strains are not present, or levels in non-treated or placebo-treated subjects, or levels in a healthy or normal subject, e.g. an age-matched subject, or the same subject before treatment. Preferably the increase will be significant, for example clinically or statistically significant, for example with a probability value of ≤0.05.

Preferably such increases (and indeed other increases, improvements or positive effects as mentioned elsewhere herein) are measurable increases, etc., (as appropriate), more preferably they are significant increases, preferably clinically significant or statistically significant increases, for example with a probability value of 0.05, when compared to an appropriate control level or value (e.g. compared to an untreated or placebo treated subject or compared to a healthy or normal subject, or the same subject before treatment).

The term "decrease" or "reduce" (or equivalent terms) as described herein includes any measurable decrease or reduction when compared with an appropriate control. Appropriate controls would readily be identified by a person skilled in the art and might include levels when strains are not present, or levels in non-treated or placebo-treated subjects, or levels in a healthy or normal subject, e.g. an age-matched subject, or the same subject before treatment. Preferably the decrease or reduction will be significant, for example clinically or statistically significant, for example with a probability value of 0.05.

Thus, preferably such decreases (and indeed other decreases, reductions or negative effects as mentioned elsewhere herein) are measurable decreases, etc., (as appropriate), more preferably they are significant decreases, preferably clinically significant or statistically significant decreases, for example with a probability value of 0.05, when compared to an appropriate control level or value (e.g. compared to an untreated or placebo treated subject or compared to a healthy or normal subject, or the same subject before treatment).

As used throughout the entire application, the terms "a" and "an" are used in the sense that they mean "at least one", "at least a first", "one or more" or "a plurality" of the referenced components or steps, except in instances wherein an upper limit is thereafter specifically stated.

In addition, where the terms "comprise", "comprises", "has" or "having", or other equivalent terms are used herein, then in some more specific embodiments these terms include the term "consists of" or "consists essentially of", or other equivalent terms. Lists "consisting of" various components and features as discussed herein can also refer to lists "comprising" the various components and features.

Other objects and advantages will be more fully apparent from the following non-limiting examples and appended claims.

EXAMPLES

Example 1

A Method for Identification of Strains Having a Gene Encoding a Cell Surface Located 5'-Nucleotidase Cultivate the bacteria on MRS plates for 16 h at 37° C. in anaerobic atmosphere. Collect 10 bacterial colonies with a sterile plastic loop and suspended in 100 microlitres of sterile water (PCR quality). (Alternative: Prepare DNA from the bacterial culture using a suitable method).

Presence of the 5'-nucleotidase gene can be examined by PCR, e.g. by using PuReTaq Ready To Go PCR beads (GE HealthCare) and any of the primer pairs described below (0.4 mM of each). Bacterial suspension or DNA preparation (0.5 microliter) should be added to the PCR mix and the PCR reaction should be performed by running the program 95° C., 5 min; 30× (95° C., 30 s; 55° C., 30 s; 72° C., 30 s); 72°, 10 min. The PCR products could be separated and visualised by using standard agarose gel electrophoresis and the sequence determined by standard Sanger sequencing (using the forward primer used for the PCR).

The gene could be detected using any of the following primers:

```
Primer pair 1 (product size 233 bp)
LrNuc1f:
                                              (SEQ ID NO: 2)
GGAACTTTGGGAAACCATGA LrNuc1r:
                                              (SEQ ID NO: 3)
CGGGCAACTTTACCATCACT Primer pair 2 (product size 212 bp)
LrNuc2f:
                                              (SEQ ID NO: 4)
TACTCGTGAAAATGCCGTTG LrNuc2r:
                                              (SEQ ID NO: 5)
GTGCCCCTGTCATTTCAACT Primer pair 3 (product size 232 bp)
LrNuc3f:
                                              (SEQ ID NO: 6)
AGCTTTACCAAATTGACCCTGA LrNuc3r:
                                              (SEQ ID NO: 7)
TTGATATTAGGCGCATCCTTTT
```

Sequences

Gene encoding Cell surface anchored 5'-nucleotidase, GenBank accession number: AEI56270.1, LPXTG-motif cell wall anchor domain protein [Lactobacillus reuteri SD2112] (SEQ ID NO: 8)
ATGAAGAATAATAGTTCAAAATATTGTTTATTGTTAGGGACAGCGCTGT
TAGGACTATATTTCCAAGCTAATAGTGTTCATGCGGATGCGACTGGTAT
CACAGCTAATGGAGAAACTACCCATAGCAATGTTACTCCAATGGTTCAG
ACTAATAAGGATGAGGCAAGTACACCGCAAACAACTACTGATTGGTCTG
ACCCGGCCAAATATCAAAGTGACATTCCAGTTCAGATTTTAGGAATCAA
TGACTTGCATGGTGGGTTAGAAACGACTGGATCAGCTACGATTGGAGAT
AAGACTTATTCGAATGCCGGAACAGTTGCACGCCTAGCTGGTAACCTTG
ATGCGGCGGAGGAAAGTTTTAAGAACGCTAATCCGACGGGAAGCTCAAT
TCGGGTAGAAGCCGGAGATATGGTTGGGGCTTCTCCAGCAAATTCTGCT
CTTCTCCAAGACGAATCAACCATGCATGCTTTAGACGCAATGCATTTTG
AAATAGGAACTTTGGGAAACCATGAGTTCGATGAAGGTTTAGCTGAGTA
TATGCGGATTGTTAATGGTGGTGAACCTACTAAACAATATAATGAAGCT
GAGATGGCCTATCCTCATGTGAAAACAGGGATTAATATCATTACTGCCA
ATGTTGTAAATAAATCTGATGGTCAAATCCCATTTGGAATGCAACCATA
CTTGATTAAAGAAATTCATACTAGTGATGGTAAAGTTGCCCGGATCGGA
TTTATTGGGATTGAAACTACTTCCCTACCAATTTTAACCTTATACGATA
ATTACAAAGATTATGATGTTTTAGACGAGGCTGAAACAATTGCAAAATA
TGATCAAATTTTACGCAAAAAAGGTGTTAACGCAATTGTAGTTCTTGCC
CATACAGGGGTTTCAACTGATAAAGATGGCAGCACTAAAGGTAATGCTG
TTGATATCATTAAGAAGCTTTACCAAATTGACCCTGATAATTCTGTCGA
CCTTTATATTGCTGGTCACTCCCACCAATATGCTAATGCTACTGTTGGA
AGTGTAAAATTAGTGCAAGCCATTTACACGGGTAAAGCTTACGATGATA
TTATCGGTTACATCGATCCAACAACTAATGATTTTGCGCCCAATAGTCT
CGTTTCACATGTCTTTCCGGTACTATCTGAAAAGGATGCGCCTAATATC
AAAACGGATGCAAATGTTACAGCAATTGTTGAAGATGCGAACAACCGAG
TAGCACCGATTATTAACAAGAAAATAGGGGAAGCTGCTACAACAGGCGA
TATTCTTGGACGACTTCATAATACTCCTACTCGTGAAAATGCCGTTGGT
GAATTAGTTGTCGATGGTCAATTATATGCCGCTCATAAAGTAGGCTTAC
CAGCTGATTTTGCGATGACTAATACAGGGGGCGTTCGTGCAGATCTGCA
TGTTAATCCTGATCGTTCCATTACATGGGGAGTGCCCAAGCAGTTCAA
CCATTTGGTAATATTTTGCGGGTAGTTGAAATGACAGGGGCACAAATCG
TTGAAGCCTTGAATCAACAATACGACGAAGATCAAGCTTACTACTTACA
GATTTCCGGGCTACATTATACTTATACTGACCAAAACGATCCTAACCAA
CCATATAAGGTCGTTCAAGTTTATGACCAACATAATCAACCGCTTGATA
TGAATAAGACTTACAATGTTGTTATTAATGACTTTTTAGCAGGTGGCGG
AGATGGCTTTTCTGCATTTAAGGGTACTAAAGTTGTCGGGATTGTTGGT
CAAGATACAGACGCGTTTATTGACTATATTACTGATATGACTAATGATG
GTAAACCAATTACTGCGCCAACAATGAACCGTAAGATTTACTTGACTGC
TGAACAAGTAGCGAAGGCTGACTCAGATTCACAGTTACAAACAGGAACT
AATCAGAACACTCAAAACGATGCTAATTCCCAGACTGAAGGAAATCAGC
TTCAAGAAGTTCCGAGCCAACCGGTATCTCCAACAGTAACCTTGCCAAC
AACAGCTGGTCAACCCGCCGAAACTGTTACACTACATGCTCAATCTAAG
CAACAAACCGTAGCTGCTAATAATCAATTAATTAATTTGACGCCTACAT
CAATTAATGGCCAAAAACAAAAAGCAGCTGACCAGCAAGCAGCTTTACC
ACAAACTAGTAACGATGAAGATCTTGCATTACTTCTTCTCGGAAGTTCA
TTAATGGCAGCAACCGGATTGACAATTATTGATCGCAAGCGTAAACATG
CTTAA Cell surface anchored 5'-nucleotidase protein, GenBank accession number: AEI56270.1, LPXTG-motif cell wall anchor domain protein [Lactobacillus reuteri SD2112] (SEQ ID NO: 9)
MKNNSSKYCLLLGTALLGLYFQANSVHADATGITANGETTHSNVTPMVQ
TNKDEASTPQTTTDWSDPAKYQSDIPVQILGINDLHGGLETTGSATIGD
KTYSNAGTVARLAGNLDAAEESFKNANPTGSSIRVEAGDMVGASPANSA
LLQDESTMHALDAMHFEIGTLGNHEFDEGLAEYMRIVNGGEPTKQYNEA
EMAYPHVKTGINIITANVVNKSDGQIPFGMQPYLIKEIHTSDGKVARIG
FIGIETTSLPILTLYDNYKDYDVLDEAETIAKYDQILRKKGVNAIVVLA -continued

| Sequences |
|---|
| HTGVSTDKDGSTKGNAVDIIKKLYQIDPDNSVDLYIAGHSHQYANATVG<br>SVKLVQAIYTGKAYDDIIGYIDPTTNDFAPNSLVSHVFPVLSEKDAPNI<br>KTDANVTAIVEDANNRVAPIINKKIGEAATTGDILGRLHNTPTRENAVG<br>ELVVDGQLYAAHKVGLPADFAMTNTGGVRADLHVNPDRSITWGSAQAVQ<br>PFGNILRVVEMTGAQIVEALNQQYDEDQAYYLQISGLHYTYTDQNDPNQ<br>PYKVVQVYDQHNQPLDMNKTYNVVINDFLAGGGDGFSAFKGTKVVGIVG<br>QDTDAFIDYITDMTNDGKPITAPTMNRKIYLTAEQVAKADSDSQLQTGT<br>NQNTQNDANSQTEGNQLQEVPSQPVSPTVTLPTTAGQPAETVTLHAQSK<br>QQTVAANNQLINLTPTSINGQKQKAADQQAALPQTSNDEDLALLLLGSS<br>LMAATGLTIIDRKRKHA |

Example 2

Procedure for Analysing 5'-Nucleotidase Activity

The Crystal Chem 5'-Nucleotidase Assay Kit (Crystal Chem, Elk Grove Village, IL, USA) was used for determining the 5'-nucleotidase activity of the bacterial cells and the fermentation supernatants. In short, the procedure was as follows.

In two steps, reagents CC1 and CC2 was added to the samples containing the bacteria or the supernatants. Reagent 1 contains AMP that was converted to adenosine by the 5'-nucleotidase enzyme from the bacteria. Adenosine was further hydrolysed into inosine and hypoxanthine by components in reagent 1. In the second step, hypoxanthine was converted to uric acid and hydrogen peroxide, which was used to generate a quinone dye that was measured kinetically at 550 nm in a spectrophotometer. The activity was determined by calculating the change in absorbance between 3 and 5 minutes and comparing with the value from a calibrator sample.

Example 3

5'-Nucleotidase Activity in *Lactobacillus reuteri* Strains

Figure 3:
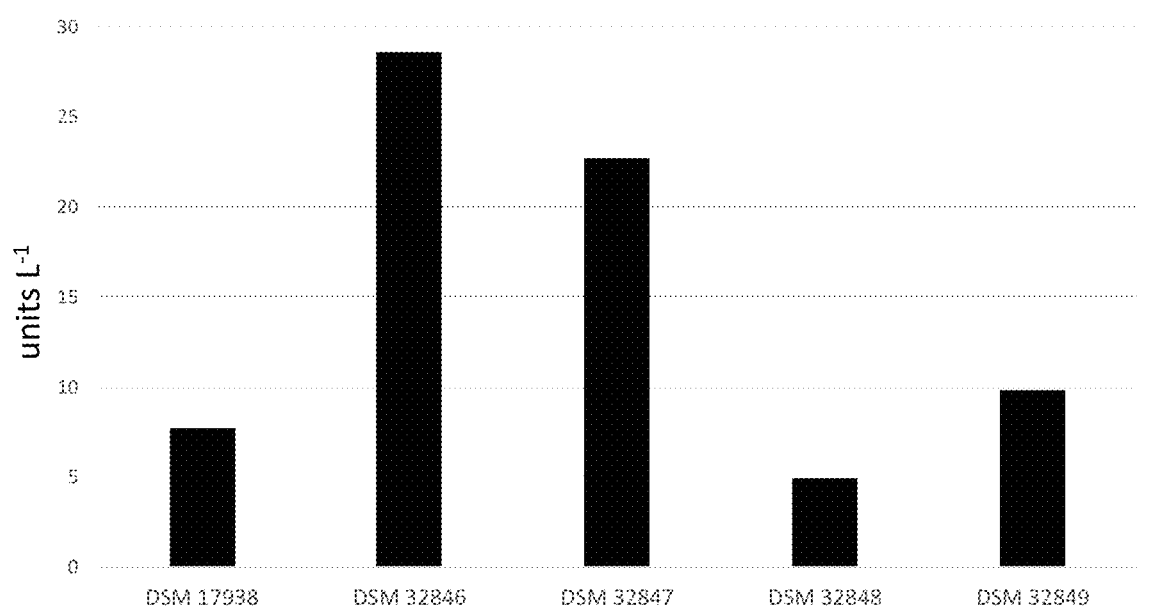
FIG. 3 shows the measurement of 5'-nucleotidase activity in the supernatant of *L. reuteri* bacterial cells.

Experimental data showing 5'-nucleotidase activity in *Lactobacillus reuteri* DSM 32846, DSM 32847, DSM 32848 and DSM 32849 as well as in *Lactobacillus reuteri* DSM 17938 (deposited under the Budapest Treaty at the DSMZ-Deutsche Sammlung von Mikroorganismen und Zellkulturen GmbH (Mascheroder Weg 1b, D-38124 Braunschweig) on 30 Jan. 2006) was generated using the method described in Example 2 above. The results are shown in FIG. 3.

Example 4

Selection of Strains

All new strains in Example 3 above, i.e. *Lactobacillus reuteri* DSM 32846, DSM 32847, DSM 32848 and DSM 32849 show 5'-nucleotidase activity in the bacterial supernatant. Analysis was carried out on the supernatant of bacterial cultures with the concentration of $10^9$ bacteria per ml.

*Lactobacillus reuteri* DSM 32846, DSM 32847, DSM 32848 and DSM 32849 have been developed/evolved for improved properties. DSM 32846 and DSM 32847 have been made to evolve to be more tolerant to bile acids and thereby survive in larger numbers in the GI-tract. DSM 32848 and DSM 32849 have evolved to adhere better to mucus, with the aim to colonize better in the GI-tract and thereby function better according to the present invention.

All strains *Lactobacillus reuteri* DSM 32846, DSM 32847, DSM 32848 and DSM 32849 are selected. Preferred strains are DSM 32846, DSM 32847 and DSM 32849.

Example 5

Effects of Probiotic Bacterial Strains on Melatonin Production in a Human Intestinal Enteroid Model Background Human intestinal enteroids (HIEs) that are derived from intestinal crypt stem cells are biologically relevant in an in vitro model of the intestinal epithelium. HIEs contain all intestinal epithelial cell types; however, similar to the human intestine, HIEs normally produce Enteroendocrine cells (EECs) in low amounts (~1%), which limits their study. To increase the number of EECs in HIEs, a lentivirus transduction was used to stably engineer jejunal HIEs with doxycycline-inducible expression of neurogenin-3 (NGN3), a transcription factor that drives EEC differentiation (tetNGN3-HIEs). In this genetically engineered cell line the number of enteroendocrine cells present in the culture increases from ≤1% to ~40%.

Material and Methods

Human Intestinal Enteroids

HIE cultures were generated from crypts isolated from the jejunal tissues of adult patients undergoing bariatric surgery. These established cultures were obtained at Baylor College of Medicine through the Texas Medical Center Digestive Diseases Center Study Design and Clinical Research Core. Three-dimensional HIE cultures were prepared from the tissue samples and maintained in culture. To increase the number of EECs in HIEs, a lentivirus transduction was used to stably engineer jejunal HIEs with doxycycline-inducible expression of neurogenin-3 (NGN3), a transcription factor that drives EEC differentiation (tetNGN3-HIEs). In this genetically engineered cell line the number of enteroendocrine cells present in the culture increases from ≤1% to ~40%. All enteroids were propagated and differentiated in 96-well monolayer form per standard protocols. More information on this enteroid line, how it is cultured and general methodology for the assay are described in Chang-Graham et al (Chang-Graham et al., Cellular and Molecular Gastroenterology and Hepatology, 2019, S2352-345X(19)30049-9, in press, online publication available).

Bacterial Strains and Preparations

In this experiment two different *Lactobacillus reuteri* strains (DSM 17938 and DSM 32846) were studied in regards to their capability of increasing the melatonin production in the intestine.

Conditioned medium (supernatant) from *Lactobacillus reuteri* DSM 17938 and *Lactobacillus reuteri* DSM 32846 grown in *Lactobacillus* Defined Media 4 (LDM4) media until they reach stationary phase was used in this study, see more details below.

A single colony of the bacterial strain was picked from an MRS agar plate and used to inoculate 10 mL of MRS broth and incubated in a tightly closed conical tube in a 37° C. water bath. After eight hours a 1:10 dilution of the culture was made and the optical density at 600 nm was read by spectrophotometer, then a 25 mL of pre-warmed LDM4 was inoculated at a starting OD of 0.1 (calculation below) and placed into the water bath to incubate for 16 hours.

OD=0.307. 1:10 Dilution=OD of 3.07

25 mL*(0.1 OD)=3.07x x=0.814 mL 814 uL was combined with 24.19 mL of LDM4

After 16 hours the culture was taken out. The final OD was 2.6. The cells were pelleted by centrifugation at 4700 rpm and the supernatant was transferred to a new 50 mL conical tube. The supernatants were stored at −20° C. overnight.

Chemicals Used

AMP=Adenosine 5'-monophosphate, 99% (Acros Organics) Code: 102790259, Lot: A0395274.

The 10 mL of stock solution (Stock solution of 2 mM=6.9 mg/ml (FW=347.224)) was made in MiliQ water and filter sterilized through a 0.22 uM filter.

Experimental Setup

Control treatments on induced enteroids:
LDM4 (culture medium),
LDM4+20 uM AMP,
LDM4+200 uM AMP Experimental treatments of DSM 32846 and DSM 17938 supernatant on induced enteroids:
DSM 32846 supernatant alone
DSM 32846 supernatant+20 uM AMP
DSM 32846 supernatant+200 uM AMP
DSM 17938 supernatant alone
DSM 17938 supernatant+20 uM AMP
DSM 17938 supernatant+200 uM AMP Before the supernatant or the other additions was ready to be applied onto the enteroids, pH was neutralized and the supernatant was filter sterilized. The pH was adjusted to 7.0 using 10-30 uL of 10M Sodium Hydroxide solution and the pH was measured by applying 2 uL of the supernatant onto pH Paper (Fisher Brand—Cat. 13-640-510 range 6.0-8.0). The supernatant was filter sterilized using a 0.22 uM filter (Thermo Scientific Nalgene Rapid Flow 0.22 uM filters Code: 00158)

100 uL (total volume) of treatment was placed on the enteroids. Incubation was 1 hour on the enteroids at 37° C., 5% $CO_2$ tissue culture incubator. Following incubation, the supernatant was removed and stored at −20° C. until downstream analysis.

Melatonin was detected by ELISA (Eagle Biosciences Inc, Amherst, NH, USA). The only step that was done prior to following the standard protocol was that the supernatants were thawed, and allowed to reach room temperature. (approximately 20-21 degrees Celsius).

Results

Figure 4:
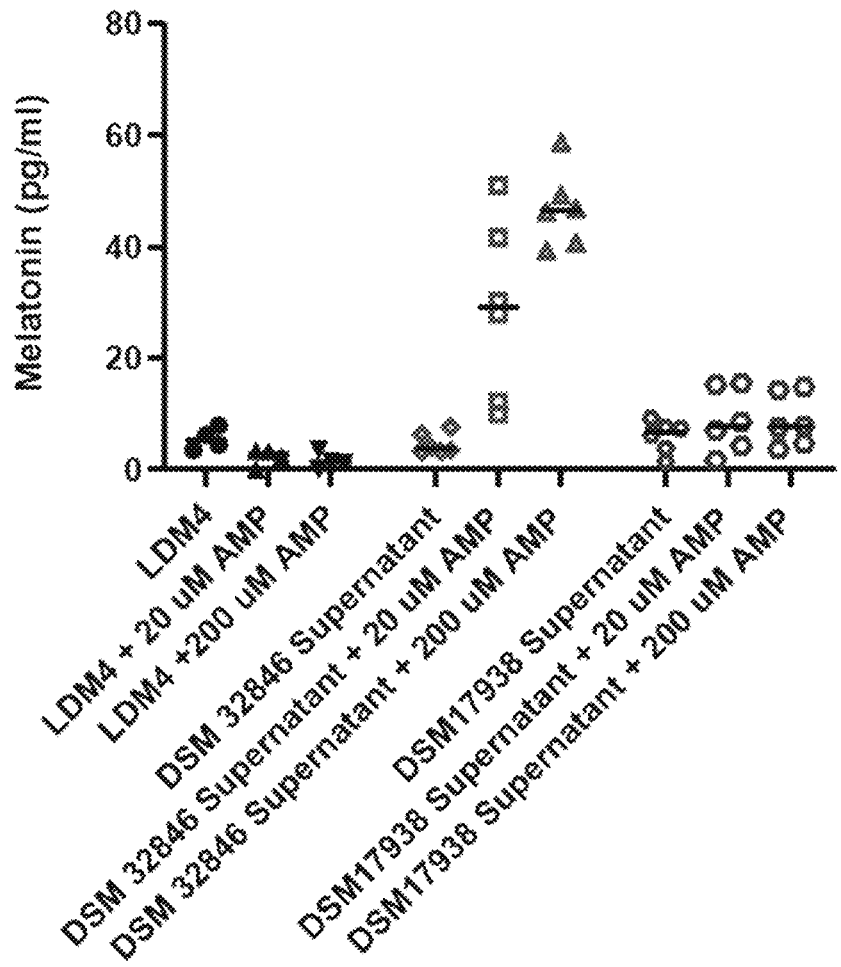
FIG. 4 shows the melatonin production in an intestinal enteroid model by the addition of supernatant of *L. reuteri* bacterial cells.

The human intestinal enteroids (HIEs) is biologically relevant as an in vitro model of the intestinal epithelium. As shown in FIG. 4 DSM 32846 alone has no significant effect, but when supplemented with AMP it shows a pronounced effect on melatonin production from the HIEs. A higher concentration of AMP gave an even higher melatonin production. DSM 17938 has an increase in melatonin production compared to the control but smaller than DSM 32846. DSM 32846 is therefore a good candidate strain for use in the production of melatonin in the intestine.

Example 6

5'-Nucleotidase Activity in *Lactobacillus reuteri* Strains

Experimental data showing 5'-nucleotidase activity in *Lactobacillus reuteri* DSM 33198 was generated using the method described in Example 2 above. The results are shown in FIG. 5A where they have been normalized in relation to the 5'-nucleotidase activity of DSM17938 (DSM17938 activity=1) from the same experiment. The same type of normalization in relation to the 5'-nucleotidase activity of DSM17938 (DSM17938 activity=1) has also been done on the results from FIG. 3 and this is presented in FIG. 5B, making it easy to compare the fold-change in 5'-nucleotidase activity in relation to DSM17938 for the different bacterial strains.

Example 7

Selection of Strains

The new strain in Example 6 above, i.e. *Lactobacillus reuteri* DSM 33198 show high 5'-nucleotidase activity in the bacterial supernatant. Analysis was carried out on the supernatant of the bacterial culture with the concentration of $10^9$ bacteria per ml.

*Lactobacillus reuteri* DSM 33198 has been developed for improved properties. The *L. reuteri* strain DSM 33198 has been modified in a multi-step selection process including a repeated freeze-drying procedure to allow it to be more tolerant and give a higher survival in the production process than its native isolate.

*Lactobacillus reuteri* DSM 33198 is selected.

The invention claimed is:

1. A bacterial strain, wherein said bacterial strain is *Lactobacillus reuteri* DSM 32846, DSM 32847, DSM 32849, or DSM 33198.

2. The bacterial strain of claim 1, wherein said bacterial strain is *Lactobacillus reuteri* DSM 32846.

3. The bacterial strain of claim 1, wherein said bacterial strain is in dried form.

4. A combination product for increasing the production of melatonin or adenosine in a subject comprising:
   (i) the *Lactobacillus reuteri* bacterial strain of claim 1; and
   (ii) a further source of melatonin and/or adenosine, or one or more substrate components or agents to increase or enhance the production or induction of melatonin and/or adenosine by said bacterial strain.

5. A method of producing or inducing the production of melatonin or adenosine in a subject comprising administering to the subject a *Lactobacillus reuteri* strain of claim 1.

6. A composition comprising at least one *Lactobacillus reuteri* strain of claim 1.

7. A method of treating irritable bowel syndrome (IBS), sleep disorders, or neurodegenerative diseases in a subject, comprising administering to the subject a therapeutically effective amount of a *Lactobacillus reuteri* strain of claim 1.

8. The method according to claim 7, wherein administering said strain produces or induces the production of adenosine and/or melatonin in the subject.

9. A method of treating infantile colic in a subject in need thereof, comprising administering to the subject a therapeutically effective amount of a *Lactobacillus reuteri* strain of claim 1.

10. The method of claim 9, wherein the subject is an infant of up to 12 months old; and/or wherein the subject is breastfed or fed with formula milk, or a combination thereof.

11. The method of claim 9, further comprising administrating at least one further substrate component or agent that increases or enhances the production or induction of melatonin and/or adenosine in the subject, wherein the at least one further agent can either be administered as a combined preparation with the *Lactobacillus reuteri* or can be administered separately.

12. The method of claim 11, wherein said at least one further agent comprises AMP (adenosine monophosphate) or a source of AMP.

13. The method of claim 9, wherein said strain is *Lactobacillus reuteri* DSM 32846.

14. The method of claim 9, wherein administering the therapeutically effective amount of the *Lactobacillus reuteri* strain produces or induces the production of melatonin and/or adenosine by at least 1.5 fold, at least 2 fold, or at least 5 fold, as compared to the levels before administration.

15. The method according to claim 9, wherein administering said strain produces or induces the production of adenosine and/or melatonin in the subject.

16. The method of claim 15, wherein administering said strain causes an increase of up to 5 fold in 5'-nucleotidase activity and/or levels of adenosine and/or levels of melatonin in the subject, as compared to the levels before administration.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: any amino acid

<400> SEQUENCE: 1

Leu Pro Xaa Thr Gly
1               5

<210> SEQ ID NO 2
<211> LENGTH: 20
<212> TYPE: DNA
<213> ORGANISM: Artificial Sequence
<220> FEATURE:
<223> OTHER INFORMATION: Primer LrNuc1f
```

<400> SEQUENCE: 2
ggaactttgg gaaaccatga                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer LrNuc1r

<400> SEQUENCE: 3
cgggcaactt taccatcact                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer LrNuc2f

<400> SEQUENCE: 4
tactcgtgaa aatgccgttg                                                    20

<210> SEQ ID NO 5
<211> LENGTH: 20
<212> TYPE: DNA
<213> ORGANISM: Artificial Sequence
<220> FEATURE:
<223> OTHER INFORMATION: Primer LrNuc2r

<400> SEQUENCE: 5
gtgcccctgt catttcaact                                                    20

<210> SEQ ID NO 6
<211> LENGTH: 22
<212> TYPE: DNA
<213> ORGANISM: Artificial Sequence
<220> FEATURE:
<223> OTHER INFORMATION: Primer LrNuc3f

<400> SEQUENCE: 6
agctttacca aattgaccct ga                                                 22

<210> SEQ ID NO 7
<211> LENGTH: 22
<212> TYPE: DNA
<213> ORGANISM: Artificial Sequence
<220> FEATURE:
<223> OTHER INFORMATION: Primer LrNuc3r

<400> SEQUENCE: 7
ttgatattag gcgcatcctt tt                                                 22

<210> SEQ ID NO 8
<211> LENGTH: 2259
<212> TYPE: DNA
<213> ORGANISM: Lactobacillus reuteri SD112

<400> SEQUENCE: 8
atgaagaata atagttcaaa atattgttta ttgttaggga cagcgctgtt aggactatat        60
ttccaagcta atagtgttca tgcggatgcg actggtatca cagctaatgg agaaactacc       120
catagcaatg ttactccaat ggttcagact aataaggatg aggcaagtac accgcaaaca       180

| | |
|---|---|
| actactgatt ggtctgaccc ggccaaatat caaagtgaca ttccagttca gattttagga | 240 |
| atcaatgact tgcatggtgg gttagaaacg actggatcag ctacgattgg agataagact | 300 |
| tattcgaatg ccggaacagt tgcacgccta gctggtaacc ttgatgcggc ggaggaaagt | 360 |
| tttaagaacg ctaatccgac gggaagctca attcgggtag aagccggaga tatggttggg | 420 |
| gcttctccag caaattctgc tcttctccaa gacgaatcaa ccatgcatgc tttagacgca | 480 |
| atgcattttg aaataggaac tttgggaaac catgagttcg atgaaggttt agctgagtat | 540 |
| atgcggattg ttaatggtgg tgaacctact aaacaatata tgaagctga tggcctat | 600 |
| cctcatgtga aaacagggat taatatcatt actgccaatg ttgtaaataa atctgatggt | 660 |
| caaatcccat ttggaatgca accatacttg attaaagaaa ttcatactag tgatggtaaa | 720 |
| gttgcccgga tcggatttat tgggattgaa actacttccc taccaatttt aaccttatac | 780 |
| gataattaca agattatga tgttttagac gaggctgaaa caattgcaaa atatgatcaa | 840 |
| attttacgca aaaaggtgt taacgcaatt gtagttcttg cccatacagg ggtttcaact | 900 |
| gataaagatg gcagcactaa aggtaatgct gttgatatca ttaagaagct ttaccaaatt | 960 |
| gaccctgata ttctgtcga cctttatatt gctggtcact cccaccaata tgctaatgct | 1020 |
| actgttggaa gtgtaaaatt agtgcaagcc atttacacgg gtaaagctta cgatgatatt | 1080 |
| atcggttaca tcgatccaac aactaatgat tttgcgccca atagtctcgt ttcacatgtc | 1140 |
| tttccggtac tatctgaaaa ggatgcgcct aatatcaaaa cggatgcaaa tgttacagca | 1200 |
| attgttgaag atgcgaacaa ccgagtagca ccgattatta acaagaaaat aggggaagct | 1260 |
| gctacaacag gcgatattct tggacgactt cataatactc ctactcgtga aaatgccgtt | 1320 |
| ggtgaattag ttgtcgatgg tcaattatat gccgctcata agtaggctt accagctgat | 1380 |
| tttgcgatga ctaatacagg gggcgttcgt gcagatctgc atgttaatcc tgatcgttcc | 1440 |
| attacatggg ggagtgccca agcagttcaa ccatttggta atattttgcg ggtagttgaa | 1500 |
| atgacagggg cacaaatcgt tgaagccttg aatcaacaat acgacgaaga tcaagcttac | 1560 |
| tacttacaga tttccgggct acattatact tatactgacc aaaacgatcc taaccaacca | 1620 |
| tataaggtcg ttcaagtttta tgaccaacat aatcaaccgc ttgatatgaa taagacttac | 1680 |
| aatgttgtta ttaatgactt tttagcaggt ggcggagatg gctttctgc atttaagggt | 1740 |
| actaaagttg tcgggattgt tggtcaagat acagacgcgt ttattgacta tattactgat | 1800 |
| atgactaatg atggtaaacc aattactgcg ccaacaatga accgtaagat ttacttgact | 1860 |
| gctgaacaag tagcgaaggc tgactcagat tcacagttac aaacaggaac taatcagaac | 1920 |
| actcaaaacg atgctaattc ccagactgaa ggaaatcagc ttcaagaagt tccgagccaa | 1980 |
| ccggtatctc caacagtaac cttgccaaca acagctggtc aacccgccga aactgttaca | 2040 |
| ctacatgctc aatctaagca acaaaccgta gctgctaata tcaattaat taatttgacg | 2100 |
| cctcacatcaa ttaatggcca aaaacaaaaa gcagctgacc agcaagcagc tttaccacaa | 2160 |
| actagtaacg atgaagatct tgcattactt cttctcggaa gttcattaat ggcagcaacc | 2220 |
| ggattgacaa ttattgatcg caagcgtaaa catgcttaa | 2259 |

<210> SEQ ID NO 9
<211> LENGTH: 752
<212> TYPE: PRT
<213> ORGANISM: Lactobacillus reuteri SD112

<400> SEQUENCE: 9

Met Lys Asn Asn Ser Ser Lys Tyr Cys Leu Leu Leu Gly Thr Ala Leu

```
1               5                   10                  15
Leu Gly Leu Tyr Phe Gln Ala Asn Ser Val His Ala Asp Ala Thr Gly
                20                  25                  30
Ile Thr Ala Asn Gly Glu Thr Thr His Ser Asn Val Thr Pro Met Val
                35                  40                  45
Gln Thr Asn Lys Asp Glu Ala Ser Thr Pro Gln Thr Thr Thr Asp Trp
                50                  55                  60
Ser Asp Pro Ala Lys Tyr Gln Ser Asp Ile Pro Val Gln Ile Leu Gly
65                  70                  75                  80
Ile Asn Asp Leu His Gly Gly Leu Glu Thr Thr Gly Ser Ala Thr Ile
                85                  90                  95
Gly Asp Lys Thr Tyr Ser Asn Ala Gly Thr Val Ala Arg Leu Ala Gly
                100                 105                 110
Asn Leu Asp Ala Ala Glu Glu Ser Phe Lys Asn Ala Asn Pro Thr Gly
                115                 120                 125
Ser Ser Ile Arg Val Glu Ala Gly Asp Met Val Gly Ala Ser Pro Ala
                130                 135                 140
Asn Ser Ala Leu Leu Gln Asp Glu Ser Thr Met His Ala Leu Asp Ala
145                 150                 155                 160
Met His Phe Glu Ile Gly Thr Leu Gly Asn His Glu Phe Asp Glu Gly
                165                 170                 175
Leu Ala Glu Tyr Met Arg Ile Val Asn Gly Glu Pro Thr Lys Gln
                180                 185                 190
Tyr Asn Glu Ala Glu Met Ala Tyr Pro His Val Lys Thr Gly Ile Asn
                195                 200                 205
Ile Ile Thr Ala Asn Val Val Asn Lys Ser Asp Gly Gln Ile Pro Phe
210                 215                 220
Gly Met Gln Pro Tyr Leu Ile Lys Glu Ile His Thr Ser Asp Gly Lys
225                 230                 235                 240
Val Ala Arg Ile Gly Phe Ile Gly Ile Glu Thr Thr Ser Leu Pro Ile
                245                 250                 255
Leu Thr Leu Tyr Asp Asn Tyr Lys Asp Tyr Asp Val Leu Asp Glu Ala
                260                 265                 270
Glu Thr Ile Ala Lys Tyr Asp Gln Ile Leu Arg Lys Lys Gly Val Asn
                275                 280                 285
Ala Ile Val Val Leu Ala His Thr Gly Val Ser Thr Asp Lys Asp Gly
                290                 295                 300
Ser Thr Lys Gly Asn Ala Val Asp Ile Lys Lys Leu Tyr Gln Ile
305                 310                 315                 320
Asp Pro Asp Asn Ser Val Asp Leu Tyr Ile Ala Gly His Ser His Gln
                325                 330                 335
Tyr Ala Asn Ala Thr Val Gly Ser Val Lys Leu Val Gln Ala Ile Tyr
                340                 345                 350
Thr Gly Lys Ala Tyr Asp Asp Ile Ile Gly Tyr Ile Asp Pro Thr Thr
                355                 360                 365
Asn Asp Phe Ala Pro Asn Ser Leu Val Ser His Val Phe Pro Val Leu
                370                 375                 380
Ser Glu Lys Asp Ala Pro Asn Ile Lys Thr Asp Ala Asn Val Thr Ala
385                 390                 395                 400
Ile Val Glu Asp Ala Asn Asn Arg Val Ala Pro Ile Ile Asn Lys Lys
                405                 410                 415
Ile Gly Glu Ala Ala Thr Thr Gly Asp Ile Leu Gly Arg Leu His Asn
                420                 425                 430
```

-continued

```
Thr Pro Thr Arg Glu Asn Ala Val Gly Glu Leu Val Val Asp Gly Gln
        435                 440                 445

Leu Tyr Ala Ala His Lys Val Gly Leu Pro Ala Asp Phe Ala Met Thr
    450                 455                 460

Asn Thr Gly Gly Val Arg Ala Asp Leu His Val Asn Pro Asp Arg Ser
465                 470                 475                 480

Ile Thr Trp Gly Ser Ala Gln Ala Val Gln Pro Phe Gly Asn Ile Leu
            485                 490                 495

Arg Val Val Glu Met Thr Gly Ala Gln Ile Val Glu Ala Leu Asn Gln
            500                 505                 510

Gln Tyr Asp Glu Asp Gln Ala Tyr Tyr Leu Gln Ile Ser Gly Leu His
        515                 520                 525

Tyr Thr Tyr Thr Asp Gln Asn Asp Pro Asn Gln Pro Tyr Lys Val Val
    530                 535                 540

Gln Val Tyr Asp Gln His Asn Gln Pro Leu Asp Met Asn Lys Thr Tyr
545                 550                 555                 560

Asn Val Val Ile Asn Asp Phe Leu Ala Gly Gly Asp Gly Phe Ser
                565                 570                 575

Ala Phe Lys Gly Thr Lys Val Val Gly Ile Val Gly Gln Asp Thr Asp
            580                 585                 590

Ala Phe Ile Asp Tyr Ile Thr Asp Met Thr Asn Asp Gly Lys Pro Ile
        595                 600                 605

Thr Ala Pro Thr Met Asn Arg Lys Ile Tyr Leu Thr Ala Glu Gln Val
    610                 615                 620

Ala Lys Ala Asp Ser Asp Ser Gln Leu Gln Thr Gly Thr Asn Gln Asn
625                 630                 635                 640

Thr Gln Asn Asp Ala Asn Ser Gln Thr Glu Gly Asn Gln Leu Gln Glu
            645                 650                 655

Val Pro Ser Gln Pro Val Ser Pro Thr Val Thr Leu Pro Thr Thr Ala
            660                 665                 670

Gly Gln Pro Ala Glu Thr Val Thr Leu His Ala Gln Ser Lys Gln Gln
        675                 680                 685

Thr Val Ala Ala Asn Asn Gln Leu Ile Asn Leu Thr Pro Thr Ser Ile
    690                 695                 700

Asn Gly Gln Lys Gln Lys Ala Ala Asp Gln Gln Ala Ala Leu Pro Gln
705                 710                 715                 720

Thr Ser Asn Asp Glu Asp Leu Ala Leu Leu Leu Gly Ser Ser Leu
            725                 730                 735

Met Ala Ala Thr Gly Leu Thr Ile Ile Asp Arg Lys Arg Lys His Ala
            740                 745                 750
```